United States Patent
Chen

(10) Patent No.: US 6,900,217 B2
(45) Date of Patent: May 31, 2005

(54) SUBSTITUTED 6,5-HETERO-BICYCLIC DERIVATIVES

(75) Inventor: Yuhpyng L. Chen, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/160,206

(22) Filed: May 30, 2002

(65) Prior Publication Data

US 2002/0151713 A1 Oct. 17, 2002

Related U.S. Application Data

(63) Continuation of application No. 09/242,682, filed on Dec. 13, 1999, now abandoned, and a continuation of application No. PCT/IB97/00922, filed on Jul. 25, 1997.
(60) Provisional application No. 60/025,039, filed on Aug. 28, 1996.

(51) Int. Cl.[7] .................... A61K 31/519; C07D 487/04
(52) U.S. Cl. .................... 514/259.3; 544/263; 544/281
(58) Field of Search ................ 544/281, 263; 514/259.3

(56) References Cited

U.S. PATENT DOCUMENTS

| | | | | |
|---|---|---|---|---|
| 6,060,478 A | * | 5/2000 | Gilligan et al. | 514/228.5 |
| 6,124,289 A | * | 9/2000 | He et al. | 514/245 |
| 6,191,131 B1 | * | 2/2001 | He et al. | 514/246 |
| 6,313,124 B1 | * | 11/2001 | He et al. | 514/246 |

FOREIGN PATENT DOCUMENTS

| | | |
|---|---|---|
| WO | 9533750 | 12/1995 |
| WO | 9635689 | 11/1996 |

* cited by examiner

*Primary Examiner*—Richard L. Raymond
(74) *Attorney, Agent, or Firm*—Peter C. Richardson; Lorraine B. Ling; Andrea E. Dorigo

(57) ABSTRACT

This invention relates to compounds of the formula

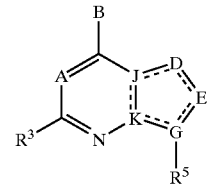

I wherein A, B, D, E, K, T, G, $R^3$ and $R^5$ are defined as in the specification, and to the pharmaceutically acceptable salts of such compounds.

10 Claims, No Drawings

SUBSTITUTED 6,5-HETERO-BICYCLIC DERIVATIVES

CROSS REFERENCE TO RELATED APPLICATIONS

This application is a Continuation of U.S. Ser. No. 09/242,682, filed Dec. 13, 1999, now abandoned, and claims benefit of U.S. Provisional Application No. 60/025,039, filed Aug. 28, 1996 and is a continuation of PCT/IB97/00922 filed Jul. 25, 1997.

BACKGROUND OF THE INVENTION

This invention relates to certain pharmaceutically active substituted 6,5-hetero-bicyclic derivatives, pharmaceutical compositions containing them and methods of administering them to subjects in need of their corticotropin releasing factor antagonist activity.

The substituted heterocyclic derivatives claimed in this case exhibit activity as corticotropin releasing factor (hormone) CRF (CRH) antagonists.

CRF antagonists are mentioned in U.S. Pat. Nos. 4,605,642 and 5,063,245 referring to peptides and pyrazolinones, respectively. They are also referred to in the following: PCT Patent Application PCT/IB95/00439, which designates the United States and was filed on Jun. 6, 1995 and published on Dec. 14, 1995; PCT Patent Application PCT/IB95/00373, which designates the United States and was filed on May 18, 1995 and published on Dec. 21, 1995; U.S. patent application Ser. No. 08/448,539, which was filed in the PCT on Nov. 12, 1993 and entered the U.S. national phase on Jun. 14, 1995; PCT Patent Application WO 95/10506, which was filed on Oct. 12, 1993 and published on Apr. 20, 1995, and U.S. patent application Ser. No. 08/481,413, which was filed in the PCT on Nov. 26, 1993 and entered the U.S. national phase on Jul. 24, 1995; U.S. patent application Ser. No. 08/254,820, which was filed on Apr. 19, 1995; Provisional U.S. patent application Ser. No. 60/008,396, which was filed on Dec. 8, 1995; and Provisional U.S. patent application Ser. No. 60/006,333, which was filed on Nov. 8, 1995. All the foregoing patent applications are incorporated herein by reference in their entireties.

The importance of CRF antagonists is set out in the literature, e.g., P. Black, *Scientific American SCIENCE & MEDICINE*, 1995, p. 16–25; T. Lovenberg et al., *Current Pharmaceutical Design*, 1995, 1, 305–316; and U.S. Pat. No. 5,063,245, which is referred to above. A recent outline of the different activities possessed by CRF antagonists is found in M. J. Owens et al., *Pharm. Rev., Vol.* 43, pages 425 to 473 (1991), also incorporated herein by reference. Based on the research described in these two and other references, CRF antagonists are effective in the treatment of a wide range of stress-related illnesses, mood disorders such as depression, major depressive disorder, single episode depression, recurrent depression, child abuse induced depression, postpartum depression, dysthemia, bipolar disorders and cyclothymia; chronic fatigue syndrome; eating disorders such as anorexia and bulimia nervosa; generalized anxiety disorder; panic disorder; phobias; obsessive-compulsive disorder, post-traumatic stress disorder, pain perception such as fibromyalgia; headache; gastrointestinal diseases; hemorrhagic stress; ulcers; stress-induced psychotic episodes; fever; diarrhea; post-operative ileus, colonic hypersensitivity; irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimer's disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiarrhetic hormone; obesity; chemical dependencies and addictions; drug and alcohol withdrawal symptoms; infertility, cancer; infertility; muscular spasms; urinary incontinence; hypoglycemia and immune dysfunctions including stress induced immune dysfunctions, immune suppression and human immunodeficiency virus infections; and stress-induced infections in humans and animals.

The compounds of this invention are also believed to be inhibitors of CRH binding protein and therefore useful in the treatment of disorders the treatment of which can be effected or facilitated by inhibiting such protein. Examples of such disorders are Alzheimer's disease and obesity.

SUMMARY OF THE INVENTION

The present invention relates to compounds of the formula

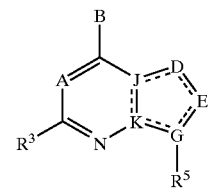

I or a pharmaceutically acceptable salt thereof, wherein
the dashed lines represent optional double bonds;
A is nitrogen or $CR^7$;
B is $-NR^1R^2$, $-CR^1R^2R^{10}$, $-C(=CR^2R^{11})R^1$, $-NHCR^1R^2R^{10}$, $-OCR^1R^2R^{10}$, $-SCR^1R^2R^{10}$, $-CR^2R^{10}NHR^1$, $-CR^2R^{10}OR^1$, $-CR^2R^{10}SR^1$ or $-COR^2$;

J and K are each independently nitrogen or carbon and both J and K are not nitrogens;

D and E are each selected, independently, from nitrogen, $CR^4$, C=O, C=S, sulfur, oxygen, $CR^4R^6$ and $NR^8$;

G is nitrogen or carbon;

the ring containing D, E, G, K, and J in formula I may be a saturated or unsaturated 5-membered ring and may optionally contain one or two double bonds and may optionally contain from one to three heteroatoms in the ring and may optionally have one or two C=O or C=S groups;

$R^1$ is $C_1$–$C_6$ alkyl optionally substituted with one or two substituents independently selected from hydroxy, fluoro, chloro, bromo, iodo, $-O-(C_1$–$C_4$ alkyl), $CF_3$, $-C(=O)$ $O-(C_1$–$C_4$alkyl), $-OC(=O)(C_1$–$C_4$ alkyl), $-OC(=O)N$ $(C_1$–$C_4$ alkyl)$(C_1$–$C_2$ alkyl), $-NHCO(C_1$–$C_4$ alkyl), $-COOH$, $-COO(C_1$–$C_4$ alkyl), $-CONH(C_1$–$C_4$ alkyl), $-CON(C_1$–$C_4$ alkyl)$(C_1$–$C_2$ alkyl), $-S(C_1$–$C_4$ alkyl), $-CN$, $-NO_2$, $-SO(C_1$–$C_4$ alkyl), $-SO_2(C_1$–$C_4$ alkyl), $-SO_2NH(C_1$–$C_4$ alkyl) and $-SO_2N(C_1$–$C_4$ alkyl)$(C_1$–$C_2$ alkyl), wherein each of the $C_1$–$C_4$ alkyl groups in the foregoing $R^1$ groups may optionally contain one or two double or triple bonds;

$R^2$ is $C_1$–$C_{12}$ alkyl which may optionally contain from one to three double or triple bonds, aryl or $(C_1$–$C_4$ alkylene) aryl, wherein said aryl and the aryl moiety of said $(C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3$–$C_8$ cycloalkyl or ($C_1$–$C_6$ alkylene)($C_3$–$C_8$ cycloalkyl), wherein one or two of the carbon atoms of said cycloalkyl and the 5 to 8 membered cycloalkyl moieties of said ($C_1$–$C_6$ alkylene)($C_3$–$C_8$ cycloalkyl) may optionally and independently be replaced by an oxygen or sulfur atom or by $NZ^2$ wherein $Z^2$ is selected from hydrogen, $C_1$–$C_4$ alkyl, benzyl and $C_1$–$C_4$ alkanoyl, and wherein each of the foregoing $R^2$ groups may optionally be substituted with from one to three substituents independently selected from chloro, fluoro, hydroxy and $C_1$–$C_4$ alkyl, or with one substituent selected from bromo, iodo, $C_1$–$C_6$ alkoxy, —OC(=O)($C_1$–$C_6$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)-CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —$NO_2$, —SO($C_1$–$C_4$ alkyl), —$SO_2$($C_1$–$C_4$ alkyl), —$SO_2$NH($C_1$–$C_4$ alkyl) and —$SO_2$N($C_1$–$C_4$ alkyl)($C_1$–$C_2$ alkyl);

—$NR^1R^2$ or —$CR^1R^2R^{10}$ may form a saturated 3 to 8 membered carbocyclic ring which may optionally contain from one to three double bonds and wherein one or two of the ring carbon atoms of such 5 to 8 membered rings may optionally and independently be replaced by an oxygen or sulfur atom or by $NZ^3$ wherein $Z^3$ is hydrogen, $C_1$–$C_4$ alkyl, benzyl or $C_1$–$C_4$ alkanoyl;

$R^3$ is hydrogen, $C_1$–$C_4$ alkyl, —O($C_1$–$C_4$ alkyl), chloro, fluoro, bromo, iodo, ($C_1$–$C_2$ alkylene)-O—($C_1$–$C_2$ alkyl), ($C_1$–$C_2$ alkylene)-OH, or —S($C_1$–$C_4$ alkyl);

each $R^4$ is, independently, hydrogen, ($C_1$–$C_6$ alkyl), fluoro, chloro, bromo, iodo, hydroxy, cyano, amino, ($C_1$–$C_2$ alkylene)-OH, $CF_3$, $CH_2SCH_3$, nitro, —O($C_1$–$C_4$ alkyl), —N($C_1$–$C_4$ alkyl)($C_1$–$C_2$ alkyl), —S($C_1$–$C_4$ alkyl), —CO ($C_1$–$C_4$ alkyl), —C(=O)H or —C(=O)O($C_1$–$C_4$ alkyl);

$R^6$ is hydrogen, methyl or ethyl;

$R^8$ is hydrogen or $C_1$–$C_4$ alkyl;

$R^5$ is phenyl, pyridyl, pyrazinyl, pyrimidyl, pyridazinyl and wherein each of the foregoing $R^5$ groups is substituted with from one to four substituents $R^{13}$ wherein one to three of said substituents may be selected, independently, from fluoro, chloro, $C_1$–$C_6$ alkyl and —O($C_1$–$C_6$ alkyl) and one of said substituents may be selected from bromo, iodo, formyl, OH, ($C_1$–$C_4$ alkylene)-OH, ($C_1$–$C_4$alkylene)-O—($C_1$–$C_2$ alkyl), —CN, —$CF_3$, —$NO_2$, —$NH_2$, —NH($C_1$–$C_4$ alkyl), —N($C_1$–$C_2$ alkyl)($C_1$–$C_6$ alkyl), —OCO($C_1$–$C_4$ alkyl), ($C_1$–$C_4$ alkylene)-O—($C_1$–$C_4$ alkyl), —S($C_1$–$C_6$ alkyl), ($C_1$–$C_4$ alkylene)-S—($C_1$–$C_4$ alkyl), —C(=O)O ($C_1$–$C_4$ alkyl), —C(=O)($C_1$–$C_4$ alkyl), —COOH, —$SO_2$NH($C_1$–$C_4$ alkyl), —$SO_2$N($C_1$–$C_2$ alkyl)($C_1$–$C_4$ alkyl), —$SO_2NH_2$, —$NHSO_2$($C_1$–$C_4$ alkyl), —S($C_1$–$C_6$ alkyl) and —$SO_2$($C_1$–$C_6$ alkyl), and wherein each of the $C_1$–$C_4$ alkyl and $C_1$–$C_6$ alkyl moieties in the foregoing $R^5$ groups may optionally have one or two double bonds;

$R^7$ is hydrogen, $C_1$–$C_4$ alkyl, halo (e.g., chloro, fluoro, iodo or bromo), hydroxy, —O($C_1$–$C_4$ alkyl), —C(=O) ($C_1$–$C_4$ alkyl), —C(=O)O($C_1$–$C_4$ alkyl), —$OCF_3$, —$CF_3$, —$CH_2OH$ or —$CH_2O$($C_1$–$C_2$ alkyl);

$R^{10}$ is hydrogen, hydroxy, methoxy or fluoro;

$R^{11}$ is hydrogen or $C_1$–$C_4$ alkyl; and with the proviso that: a) when both J and K are carbon and D is $CR^4$ and E is nitrogen, then G can not be nitrogen; b) when both J and K are carbons and D and G are nitrogens, then E can not be $CR^4$ or C=O or C=S; (c) when both J and K are carbons and D and E are carbons, then G can not be nitrogen; (d) when G is carbon, it must be double bonded to E; and (e) in the ring containing J, K, D, E and G, there can not be two double bonds adjacent to each other.

and the pharmaceutically acceptable salts of such compounds.

When the ring containing D, E, G, K and J is a 5-membered heteroaromatic ring, it may be, e.g., pyrazolo, imidazolo, thieno, furano, thiazolo, oxazolo, triazolo or thiadiazolo.

The term "alkyl", as used herein, unless otherwise indicated, includes saturated monovalent hydrocarbon radicals having straight branched or cyclic moieties or combinations thereof.

The term "alkoxy", as used herein, unless otherwise indicated, means —O-alkyl, where "alkyl" is defined as above.

Examples of more specific embodiments of formula I are the following, wherein $(R)_n$ represents from zero to two substituents, wherein such substitutents are as defined above in the definition of formula I.

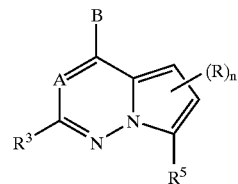

I-A

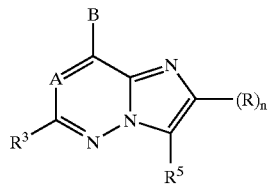

I-B

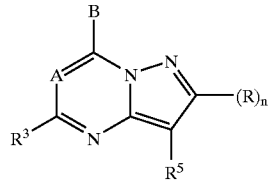

I-E

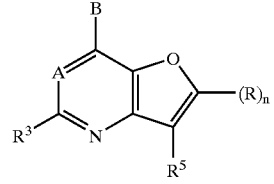

I-J

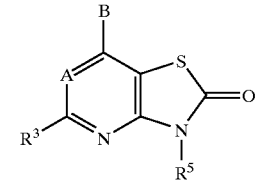

I-K

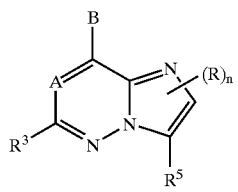 I-C
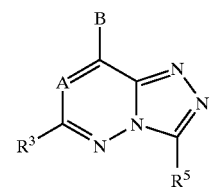 I-D
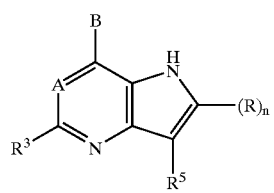 I-G
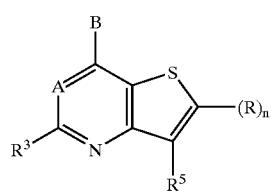 I-H
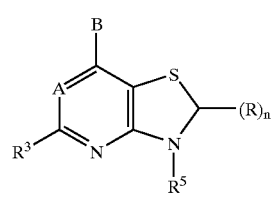 I-L
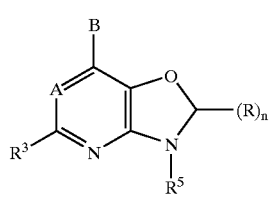 I-M
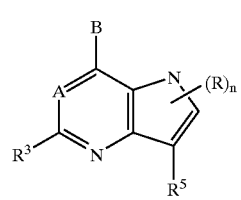 I-N
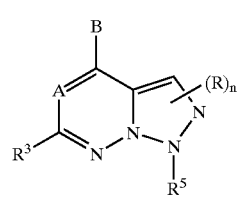 I-O
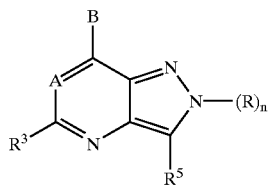 I-R
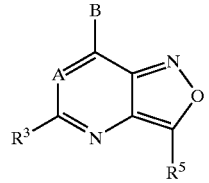 I-S
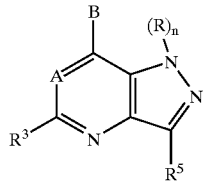 I-V
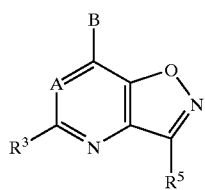 I-W
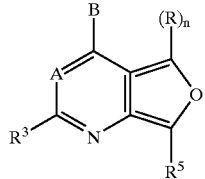 I-P
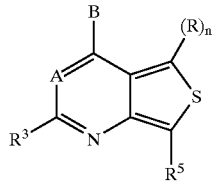 I-Q
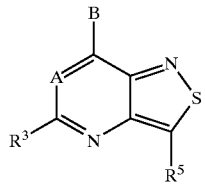 I-T
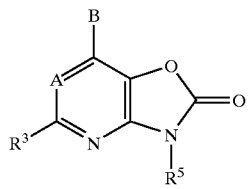 I-U

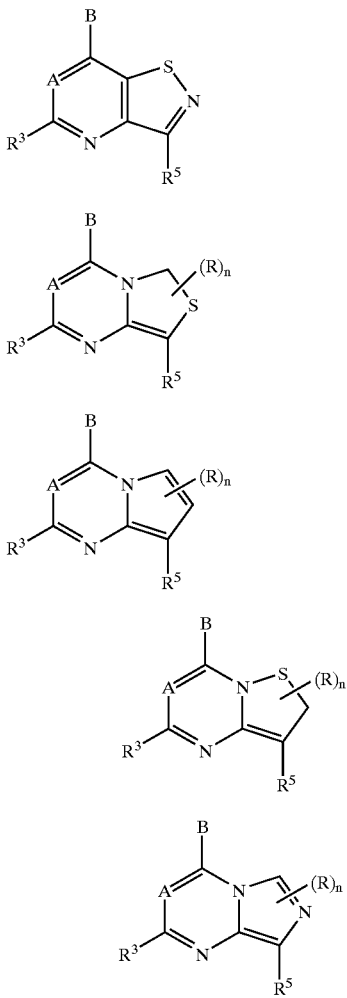

More specific embodiments of this invention include compounds of the above formula I wherein B is —CHR$^1$R$^2$, —NR$^1$R$^2$, —NHCHR$^1$R$^2$, —OCHR$^1$R$^2$ or —SCHR$^1$R$^2$, and R$^1$ is C$_1$–C$_6$ alkyl, which may optionally be substituted with one hydroxy, fluoro, CF$_3$ or C$_1$–C$_4$ alkoxy group and which may optionally contain one double or triple bond; and R$^2$ is benzyl or C$_1$–C$_6$ alkyl, which may optionally contain one double or triple bond, wherein said C$_1$–C$_6$ alkyl and the phenyl moiety of said benzyl may optionally be substituted with one fluoro, CF$_3$, C$_1$–C$_2$ alkyl, C$_1$–C$_2$ alkoxy or chloro group.

Other more specific embodiments of this invention include compounds of formula I wherein R$^3$ is methyl, ethyl, chloro or methoxy; R$^4$ and R$^6$ are selected from hydrogen, methyl and ethyl; R$^5$ is di- or tri-substituted phenyl, pyridyl, or pyrimidyl, in which the two or three substitutents on said phenyl, pyridyl or pyrimidyl are selected, independently, from C$_1$–C$_4$ alkyl, —O—(C$_1$–C$_4$ alkyl), (C$_1$–C$_2$ alkyl)-O—(C$_1$–C$_4$ alkyl), —CF$_3$, OCF$_3$, —CHO, —(C$_1$–C$_4$ alkyl)-OH, cyano, chloro, fluoro, bromo and iodo, wherein each of the forgoing C$_1$–C$_4$ alkyl groups may optionally contain one double or triple bond;

Other more specific embodiments of this invention include compounds of the formula I wherein B is or contains an NR$^1$R$^2$ or CR$^1$R$^2$R$^{10}$ moiety which forms a saturated or unsaturated 5-membered carbocyclic ring wherein one of the ring carbons may optionally be replaced by a sulfur or oxygen atom.

Other more specific embodiments of this invention include compounds of the formula I wherein A is nitrogen or CR$^7$ and R$^7$ is hydrogen or methyl.

Other more specific embodiments of this invention include compounds of the formula I wherein B is —CR$^1$R$^2$R$^{10}$, —C(=CR$^2$R$^{11}$)R$^1$, —OCR$^1$R$^2$R$^{10}$, —SCR$^1$R$^2$R$^{10}$, CR$^2$R$^{10}$NHR$^1$, CR$^2$R$^{10}$OR$^1$, —CR$^2$R$^{10}$SR$^1$ or —COR$^2$.

Other more specific embodiments of this invention include compounds of the formula I wherein A is CH, J and K are carbon and D, E, and G are nitrogen;

Other more specific embodiments of this invention include compounds of the formula I wherein J and D are nitrogen, K and G are carbon, and E is CH, CCH$_3$, or CC$_2$H$_5$.

Other more specific embodiments of this invention include compounds of the formula I wherein B contains a —NR$^1$R$^2$ or —CR$^1$R$^2$R$^{10}$ moiety that is a saturated or unsaturated three to five membered ring.

Other more specific embodiments of this invention include compounds of the formula I wherein J and K are carbon, and D—E—G is O—C(CH$_3$)=C, O—CH=C, S—C(CH$_3$)=C, S—CH=C, N(CH$_3$)—C(CH$_3$)=C, N(CH$_3$)—CH=C, O—N=C, S—N=C, N(CH$_3$)—N=C, O—CH$_2$N, S—CH$_2$N, or NH—C(C$_1$–C$_2$alkyl)=C.

Examples of preferred compounds of the formula I:
7-(1-ethyl-propoxy)-5-methyl-3-(2,4,6-trimethyl-phenyl)-pyrazolo[1,5-a]pyrimidine;
[2,5-dimethyl-3-(2,4,6-trimethyl-phenyl)-pyrazolo[1,5-a]pyrimidin-7-yl]-(1-ethyl-propyl)-amine;
(1-ethyl-propyl)-[5-methyl-3-(2,4,6-trimethyl-phenyl)-pyrazolo[1,5-a]pyrimidin-7-yl]-amine;
7-(1-ethyl-propoxy)-2,5-dimethyl-3-(2,4,6-trimethyl-phenyl)-pyrazolo[1,5-a]pyrimi-dine;
[2,5-dimethyl-3-(2,4,6-trimethyl-phenyl)-pyrazolo[1,5-a]pyrimidin-7-yl]-ethyl-propyl-amine;
[6-bromo-5-bromomethyl-3-(2,4,6-trimethyl-phenyl)-3H-[1,2,3]triazolo[4,5-b]-pyridin-7-yl]-(1-ethyl-propyl)-amine;
(1-ethyl-propyl)-[5-methyl-3-(2,4,6-trimethyl-phenyl)-3H-[1,2,3]triazolo[4,5-b]-pyridin-7-yl]-amine;
[6-bromo-5-methyl-3-(2,4,6-trimethyl-phenyl)-3H-[1,2,3]triazolo[4,5-b]pyridin-7-yl]-(1-ethyl-propyl)-methyl-amine; and
7-(1-ethyl-propoxy)-5-methyl-3-(2,4,6-trimethyl-phenyl)-3H-[1,2,3]triazolo[4,5-b]-pyridine.

Other compounds of formula I include the following:
4-(1-ethyl-propoxy)-2,7-dimethyl-8-(2,4,6-trimethyl-phenyl)-pyrrolo[1,2-a]-pyrimidine;
(1-ethyl-propyl)-[5-methyl-3-(2,4,6-trimethyl-phenyl)-pyrazolo[1,5-a]pyrimidin-7-yl]-amine;
[3-(4-bromo-2,6-dimethyl-phenyl)-5-methyl-pyrazolo[1,5-a]pyrimidin-7-yl]-(1-ethyl-propyl)-amine;
butyl-ethyl-[5-methyl-3-(2,4,6-trimethyl-phenyl)-pyrazolo[1,5-a]pyrimidin-7-yl]-amine;
3-(4-bromo-2,6-dimethyl-phenyl)-7-(1-ethyl-propoxy)-5-methyl-pyrazolo[1,5-a]-pyrimidine;
[2,7-dimethyl-8-(2,4,6-trimethyl-phenyl)-pyrrolo[1,2-a]pyrimidin-4-yl]-diethyl-amine;
[2,7-dimethyl-8-(2,4,6-trimethyl-phenyl)-pyrrolo[1,2-a]pyrimidin-4-yl]-ethyl-propyl-amine;
[8-(4-chloro-2,6-dimethyl-phenyl)-2,7-dimethyl-pyrrolo[1,2-a]pyrimidin-4-yl]-ethyl-propyl-amine;
[8-(4-chloro-2,6-dimethyl-phenyl)-2,7-dimethyl-pyrrolo[1,2-a]pyrimidin-4-yl]-diethyl-amine;
[8-(4-chloro-2,6-dimethyl-phenyl)-2,6-dimethyl-pyrrolo[1,2-a]pyrimidin-4-yl]-diethyl-amine;

[2,6-dimethyl-8-(2,4,6-trimethyl-phenyl)-pyrrolo[1,2-a]pyrimidin-4-yl]-diethyl-amine;
[2,6-dimethyl-8-(2,4,6-trimethyl-phenyl)-pyrrolo[1,2-a]pyrimidin-4-yl]-ethyl-propyl-amine;
butyl-[2,6-dimethyl-8-(2,4,6-trimethyl-phenyl)-pyrrolo[1,2-a]pyrimidin-4-yl]-ethyl-amine;
[2,6-dimethyl-8-(2,4,6-trimethyl-phenyl)-pyrrolo[1,2-a]pyrimidin-4-yl]-(1-ethyl-propyl)-amine;
[8-(4-chloro-2,6-dimethyl-phenyl)-2,6-dimethyl-pyrrolo[1,2-a]pyrimidin-4-yl]-(1-ethyl-propyl)-amine;
8-(4-chloro-2,6-dimethyl-phenyl)-4-(1-ethyl-propoxy)-2,6-dimethyl-pyrrolo[1,2-a]-pyrimidine;
4-(1-ethyl-propoxy)-2,6-dimethyl-8-(2,4,6-trimethyl-phenyl)-pyrrolo[1,2-a]-pyrimidine;
4-(1-ethyl-propoxy)-2-methyl-8-(2,4,6-trimethyl-phenyl)-pyrrolo[1,2-a]pyrimidine;
(1-ethyl-propyl)-[2-methyl-8-(2,4,6-trimethyl-phenyl)-pyrrolo[1,2-a]pyrimidin-4-yl]-amine;
butyl-ethyl-[2-methyl-8-(2,4,6-trimethyl-phenyl)-pyrrolo[1,2-a]pyrimidin-4-yl]-amine;
butyl-ethyl-[5-methyl-3-(2,4,6-trimethyl-phenyl)-2H-isothiazolo[2,3-a]-pyrimidin-7-yl]-amine;
(1-ethyl-propyl)-[5-methyl-3-(2,4,6-trimethyl-phenyl)-2H-isothiazolo[2,3-a]-pyrimidin-7-yl]-amine;
7-(1-ethyl-propoxy)-5-methyl-3-(2,4,6-trimethyl-phenyl)-2H-isothiazolo[2,3-a]-pyrimidine;
4-(1-ethyl-propoxy)-2-methyl-8-(2,4,6-trimethyl-phenyl)-imidazo[1,5-a]-pyrimidine;
(1-ethyl-propyl)-[2-methyl-8-(2,4,6-trimethyl-phenyl)-imidazo[1,5-a]pyrimidin-4-yl]-amine;
[2,6-dimethyl-8-(2,4,6-trimethyl-phenyl)-imidazo[1,5-a]pyrimidin-4-yl]-(1-ethyl-propyl)-amine;
4-(1-ethyl-propoxy)-2,6-dimethyl-8-(2,4,6-trimethyl-phenyl)-imidazo[1,5-a]-pyrimidine;
4-(1-ethyl-propoxy)-2,6-dimethyl-8-(2,4,6-trimethyl-phenyl)-6,7-dihydro-imidazo[1,5-a]pyrimidine;
4-(1-ethyl-propoxy)-2,6-dimethyl-8-(2,4,6-trimethyl-phenyl)-thiazolo[3,4-a]-pyrimidine;
4-(1-ethyl-propoxy)-2-methyl-7-(2,4,6-trimethyl-phenyl)-pyrrolo[1,2-b]pyridazine;
4-(1-ethyl-propoxy)-2,5-dimethyl-7-(2,4,6-trimethyl-phenyl)-pyrrolo[1,2-b]-pyridazine;
4-(1-ethyl-propoxy)-2,6-dimethyl-7-(2,4,6-trimethyl-phenyl)-pyrrolo[1,2-b]; pyridazine;
4-(1-ethyl-propoxy)-2,5,6-trimethyl-7-(2,4,6-trimethyl-phenyl)-pyrrolo[1,2-b]-pyridazine;
[2,5-dimethyl-7-(2,4,6-trimethyl-phenyl)-pyrrolo[1,2-b]pyridazin-4-yl]-(1-ethyl-propyl)-amine;
(1-ethyl-propyl)-[2-methyl-7-(2,4,6-trimethyl-phenyl)-pyrrolo[1,2-b]pyridazin-4-yl]-amine;
[2,6-dimethyl-3-(2,4,6-trimethyl-phenyl)-imidazo[1,2-b]pyridazin-8-yl]-(1-ethyl-propyl)-amine;
8-(1-ethyl-propoxy)-2,6-dimethyl-3-(2,4,6-trimethyl-phenyl)-imidazo[1,2-b]-pyridazine;
8-(1-ethyl-propoxy)-6-methyl-3-(2,4,6-trimethyl-phenyl)-imidazo[1,2-b]pyridazine;
(1-ethyl-propyl)-[6-methyl-3-(2,4,6-trimethyl-phenyl)-imidazo[1,2-b]pyridazin-8-yl]-amine;
(1-ethyl-propyl)-[2-methyl-7-(2,4,6-trimethyl-phenyl)-imidazo[1,5-b]pyridazin-4-yl]-amine;
[2,5-dimethyl-7-(2,4,6-trimethyl-phenyl)-imidazo[1,5-b]pyridazin-4-yl]-(1-ethyl-propyl)-amine;
4-(1-ethyl-propoxy)-2,5-dimethyl-7-(2,4,6-trimethyl-phenyl)-imidazo[1,5-b]-pyridazine-b]pyridazine;
butyl-[2,5-dimethyl-7-(2,4,6-trimethyl-phenyl)-imidazo[1,5-b]pyridazin-4-yl]-ethyl-amine;
[2,5-dimethyl-7-(2,4,6-trimethyl-phenyl)-imidazo[1,5-b]pyridazin-4-yl]-ethyl-propyl-amine;
[2,5-dimethyl-7-(2,4,6-trimethyl-phenyl)-imidazo[1,5-b]pyridazin-4-yl]-diethyl-amine;
diethyl-[6-methyl-3-(2,4,6-trimethyl-phenyl)-[1,2,4]triazolo[4,3-b]pyridazin-8-yl]-amine;
ethyl-[6-methyl-3-(2,4,6-trimethyl-phenyl)-[1,2,4]triazolo[4,3-b]pyridazin-8-yl]-propyl-amine;
butyl-ethyl-[6-methyl-3-(2,4,6-trimethyl-phenyl)-[1,2,4]triazolo[4,3-b]pyridazin-8-yl]-amine;
(1-ethyl-propyl)-[6-methyl-3-(2,4,6-trimethyl-phenyl)-[1,2,4]triazolo[4,3-b]-pyridazin-8-yl]-amine;
8-(1-ethyl-propoxy)-6-methyl-3-(2,4,6-trimethyl-phenyl)-[1,2,4]triazolo[4,3-b]-pyridazine;
7-(1-ethyl-propoxy)-1,5-dimethyl-3-(2,4,6-trimethyl-phenyl)-1H-pyrrolo[3,2-b]-pyridine;
7-(1-ethyl-propoxy)-1,2,5-trimethyl-3-(2,4,6-trimethyl-phenyl)-1H-pyrrolo[3,2-b]-pyridine;
(1-ethyl-propyl)-[1,2,5-trimethyl-3-(2,4,6-trimethyl-phenyl)-1H-pyrrolo[3,2-b]-pyridin-7-yl]-amine;
[1,5-dimethyl-3-(2,4,6-trimethyl-phenyl)-1H-pyrrolo[3,2-b]pyridin-7-yl]-(1-ethyl-propyl)-amine;
butyl-[1,5-dimethyl-3-(2,4,6-trimethyl-phenyl)-1H-pyrrolo[3,2-b]pyridin-7-yl]-ethyl-amine;
[1,5-dimethyl-3-(2,4,6-trimethyl-phenyl)-1H-pyrrolo[3,2-b]pyridin-7-yl]-ethyl-propyl-amine;
[1,5-dimethyl-3-(2,4,6-trimethyl-phenyl)-1H-pyrrolo[3,2-b]pyridin-7-yl]-diethyl-amine;
ethyl-[5-methyl-3-(2,4,6-trimethyl-phenyl)-3H-[1,2,3]triazolo[4,5-b]pyridin-7-yl]-propyl-amine;
butyl-ethyl-[5-methyl-3-(2,4,6-trimethyl-phenyl)-3H-[1,2,3]triazolo[4,5-b]pyridin-7-yl]-amine;
diethyl-[5-methyl-3-(2,4,6-trimethyl-phenyl)-3H-[1,2,3]triazolo[4,5-b]pyridin-7-yl]-amine;
[3-(4-bromo-2,6-dimethyl-phenyl)-5-methyl-3H-[1,2,3]triazolo[4,5-b]pyridin-7-yl]-(1-ethyl-propyl)-amine;
[3-(4-chloro-2,6-dimethyl-phenyl)-5-methyl-3H-[1,2,3]triazolo[4,5-b]pyridin-7-yl]-(1-ethyl-propyl)-amine;
3-(4-chloro-2,6-dimethyl-phenyl)-7-(1-ethyl-propoxy)-5-methyl-3H-[1,2,3]triazolo[4,5-b]pyridine;
3-(4-bromo-2,6-dimethyl-phenyl)-7-(1-ethyl-propoxy)-5-methyl-3H-[1,2,3]triazolo[4,5-b]pyridine;
7-(1-ethyl-propoxy)-5-methyl-3-(2,4,6-trimethyl-phenyl)-isothiazolo[4,5-b]pyridine;
(1-ethyl-propyl)-[5-methyl-3-(2,4,6-trimethyl-phenyl)-isothiazolo[4,5-b]pyridin-7-yl]-amine;
(1-ethyl-propyl)-[5-methyl-3-(2,4,6-trimethyl-phenyl)-isoxazolo[4,5-b]pyridin-7-yl]-amine;
7-(1-ethyl-propoxy)-5-methyl-3-(2,4,6-trimethyl-phenyl)-isoxazolo[4,5-b]pyridine;
7-(1-ethyl-propoxy)-5-methyl-3-(2,4,6-trimethyl-phenyl)-thieno[3,2-b]pyridine;
7-(1-ethyl-propoxy)-2,5-dimethyl-3-(2,4,6-trimethyl-phenyl)-thieno[3,2-b]pyridine;
[2,5-dimethyl-3-(2,4,6-trimethyl-phenyl)-thieno[3,2-b]pyridin-7-yl]-(1-ethyl-propyl)-amine;
(1-ethyl-propyl)-[5-methyl-3-(2,4,6-trimethyl-phenyl)-thieno[3,2-b]pyridin-7-yl]-amine;
(1-ethyl-propyl)-[5-methyl-3-(2,4,6-trimethyl-phenyl)-furo[3,2-b]pyridin-7-yl]-amine;
[2,5-dimethyl-3-(2,4,6-trimethyl-phenyl)-furo[3,2-b]pyridin-7-yl]-(1-ethyl-propyl)-amine;
7-(1-ethyl-propoxy)-2,5-dimethyl-3-(2,4,6-trimethyl-phenyl)-furo[3,2-b]pyridine;
7-(1-ethyl-propoxy)-5-methyl-3-(2,4,6-trimethyl-phenyl)-furo[3,2-b]pyridine;
4-(1-ethyl-propoxy)-2,5-dimethyl-7-(2,4,6-trimethyl-phenyl)-6H-pyrrolo[3,4-b]-pyridine;
4-(1-ethyl-propoxy)-2,5,6-trimethyl-7-(2,4,6-trimethyl-phenyl)-6H-pyrrolo[3,4-b]-pyridine;

(1-ethyl-propyl)-[2,5,6-trimethyl-7-(2,4,6-trimethyl-phenyl)-6H-pyrrolo[3,4-b]pyridin-4-yl]-amine;

[1,5-dimethyl-3-(2,4,6-trimethyl-phenyl)-2-thia-4-aza-inden-7-yl]-(1-ethyl-propyl)-amine;

7-(1-ethyl-propoxy)-1,5-dimethyl-3-(2,4,6-trimethyl-phenyl)-2-thia-4-aza-indene;

4-(1-ethyl-propoxy)-2,5-dimethyl-7-(2,4,6-trimethyl-phenyl)-furo[3,4-b]pyridine;

[2,5-dimethyl-7-(2,4,6-trimethyl-phenyl)-furo[3,4-b]pyridin-4-yl]-(1-ethyl-propyl)-amine;

[2,5-dimethyl-3-(2,4,6-trimethyl-phenyl)-2H-pyrazolo[4,3-b]pyridin-7-yl]-(1-ethyl-propyl)-amine;

7-(1-ethyl-propoxy)-2,5-dimethyl-3-(2,4,6-trimethyl-phenyl)-2H-pyrazolo[4,3-b]-pyridine;

7-(1-ethyl-propoxy)-5-methyl-3-(2,4,6-trimethyl-phenyl)-isothiazolo[4,3-b]pyridine;

(1-ethyl-propyl)-[5-methyl-3-(2,4,6-trimethyl-phenyl)-isothiazolo[4,3-b]pyridin-7-yl]-amine;

(1-ethyl-propyl)-[5-methyl-3-(2,4,6-trimethyl-phenyl)-3H-[1,2,3]triazolo[4,5-d]-pyrimidin-7-yl]-amine;

diethyl-[5-methyl-3-(2,4,6-trimethyl-phenyl)-3H-[1,2,3]triazolo[4,5-d]pyrimidin-7-yl]-amine;

ethyl-[5-methyl-3-(2,4,6-trimethyl-phenyl)-3H-[1,2,3]triazolo[4,5-d]pyrimidin-7-yl]-propyl-amine;

butyl-ethyl-[5-methyl-3-(2,4,6-trimethyl-phenyl)-3H-[1,2,3]triazolo[4,5-d]-pyrimidin-7-yl]-amine;

[2,5-dimethyl-3-(2,4,6-trimethyl-phenyl)-pyrazolo[1,5-a]pyrimidin-7-yl]-diethyl-amine;

butyl-[2,5-dimethyl-3-(2,4,6-trimethyl-phenyl)-pyrazolo[1,5-a]pyrimidin-7-yl]-ethyl-amine;

butyl-ethyl-[5-methyl-3-(2,4,6-trimethyl-phenyl)-pyrazolo[1,5-a]pyrimidin-7-yl]-amine;

ethyl-[5-methyl-3-(2,4,6-trimethyl-phenyl)-pyrazolo[1,5-a]pyrimidin-7-yl]-propyl-amine;

diethyl-[5-methyl-3-(2,4,6-trimethyl-phenyl)-pyrazolo[1,5-a]pyrimidin-7-yl]-amine;

[3-(4-chloro-2,6-dimethyl-phenyl)-5-methyl-pyrazolo[1,5-a]pyrimidin-7-yl]-(1-ethyl-propyl)-amine;

[3-(4-chloro-2,6-dimethyl-phenyl)-5-methyl-pyrazolo[1,5-a]pyrimidin-7-yl]-(1-ethyl-propyl)-amine;

3-(4-chloro-2,6-dimethyl-phenyl)-7-(1-ethyl-propoxy)-5-methyl-pyrazolo[1,5-a]-pyrimidine;

8-(4-chloro-2,6-dimethyl-phenyl)-4-(1-ethyl-propoxy)-2-methyl-pyrazolo[1,5-a]-[1,3,5]triazine;

(1-ethyl-propyl)-[2-methyl-8-(2,4,6-trimethyl-phenyl)-pyrazolo[1,5-a][1,3,5]triazin-4-yl]-amine;

4-(1-ethyl-propoxy)-2-methyl-8-(2,4,6-trimethyl-phenyl)-pyrazolo[1,5-a][1,3,5]-triazine;

4-(1-ethyl-propoxy)-2,7-dimethyl-8-(2,4,6-trimethyl-phenyl)-pyrazolo[1,5-a][1,3,5]-triazine;

[2,7-dimethyl-8-(2,4,6-trimethyl-phenyl)-pyrazolo[1,5-a][1,3,5]triazin-4-yl]-(1-ethyl-propyl)-amine;

[1,5-dimethyl-3-(2,4,6-trimethyl-phenyl)-1H-pyrazolo[4,3-b]pyridin-7-yl]-(1-ethyl-propyl)-amine;

7-(1-ethyl-propoxy)-1,5-dimethyl-3-(2,4,6-trimethyl-phenyl)-1H-pyrazolo[4,3-b]-pyridine;

7-(1-ethyl-propoxy)-5-methyl-3-(2,4,6-trimethyl-phenyl)-isothiazolo[4,5-b]-pyridine;

(1-ethyl-propyl)-[5-methyl-3-(2,4,6-trimethyl-phenyl)-isothiazolo[4,5-b]pyridin-7-yl]-amine;

1,5-dimethyl-3-(2,4,6-trimethyl-phenyl)-7-(1-ethyl-propoxy)-1H-pyrrolo[3,2-b]pyridine;

1,5-dimethyl-3-(2,6-dimethyl-4-chloro-phenyl)-7-(1-ethyl-propoxy)-1H-pyrrolo[3,2-b]pyridine;

2,5-dimethyl-3-(2,4,6-trimethyl-phenyl)-7-(1-ethyl-propoxy)-1H-pyrrolo[3,2-b]pyridine;

2,5-dimethyl-3-(2,6-dimethyl-4-chloro-phenyl)-7-(1-ethyl-propoxy)-1H-pyrrolo[3,2-b]pyridine;

7-(1-cyclopropylmethyl-propoxy)-1,5-dimethyl-3-(2,4,6-trimethyl-phenyl)-1H-pyrrolo[3,2-b]pyridine;

7-(1-cyclopropylmethyl-propoxy)-1,5-dimethyl-3-(2,6-dimethyl-4-chloro-phenyl)-1H-pyrrolo[3,2-b]pyridine;

1,5-dimethyl-3-(2,4,6-trimethyl-phenyl)-7-(tetrahydro-furan-3-yloxy)-1H-pyrrolo[3,2-b]pyridine;

1,5-dimethyl-3-(2,4,6-trimethyl-phenyl)-7-(S)-(tetrahydro-furan-3-yloxy)-1H-pyrrolo[3,2-b]pyridine;

1,5-dimethyl-3-(2,4,6-trimethyl-phenyl)-7-(1-propyl-butoxy)-1H-pyrrolo[3,2-b]pyridine;

7-sec-butylsulfanyl-1,5-dimethyl-3-(2,4,6-trimethyl-phenyl)-1H-pyrrolo[3,2-b]pyridine;

cyclopropylmethyl-[2,5-dimethyl-7-(2,4,6-trimethyl-phenyl)-5H-pyrrolo[3,2-b]pyrimidin-4-yl]-propyl-amine;

2-[1,5-dimethyl-3-(2,4,6-trimethyl-phenyl)-1H-pyrrolo[3,2-b]pyridin-7-ylamino]-butan-1-ol;

1,5-dimethyl-7-thiazolidin-3-yl-3-(2,4,6-trimethyl-phenyl)-1H-pyrrolo[3,2-b]pyridine;

[1,5-dimethyl-3-(2,4,6-trimethyl-phenyl)-1H-pyrrolo[3,2-b]pyridin-7-yl]-ethyl-(2,2,2-trifluoro-ethyl)-amine;

cyclopropylmethyl-[1,5-dimethyl-3-(2,4,6-trimethyl-phenyl)-1H-pyrrolo[3,2-b]pyridin-7-yl]-propyl-amine;

(1-ethyl-propyl)-[5-methyl-3-(2,4,6-trimethyl-phenyl)-isoxazolo[4,5-b]pyridin-7-yl]-amine; and 7-(1-ethyl-propoxy)-5-methyl-3-(2,4,6-trimethyl-phenyl)-isoxazolo[4,5-b]-pyridine.

This invention also relates to a pharmaceutical composition for the treatment, prevention or inhibition of (a) a disorder the treatment of which can be effected or facilitated by antagonizing CRF, including but not limited to disorders induced or facilitated by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies and addictions (e.g., dependencies on alcohol, nicotine, cocaine, heroin, benzodiazepines, or other drugs); drug and alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfract dementia; amyotrophic lateral sclerosis; hypertension; tachycardia; congestive heart failure; osteoporosis; premature birth; and hypoglycemia in a mammal, including a human, comprising an amount of a compound of the formula I, or a pharmaceutically acceptable salt thereof, that is effective in the treatment of such disorder, and a pharmaceutically acceptable carrier.

The invention also relates to a method for the treatment, prevention or inhibition of (a) a disorder the treatment of which can be effected or facilitated by antagonizing CRF, including but not limited to disorders induced or facilitator by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome; Crohn's disease; spastic colon; post operative ileus; ulcer; diarrhea; stress-induced fever; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, nicotine, cocaine, heroin, benzodiazepines, or other drugs); drug and alcohol withdrawal symptoms; hypertension; tachycardia; congestive heart failure; osteoporosis; premature birth; and hypoglycemia in a mammal, including a human, comprising administering to a subject in need of said treatment an amount of a compound of the formula I, or a pharmaceutically acceptable salt thereof, that is effective in treating such disorder.

This invention also relates to a method of treating or preventing a disorder or condition, the treatment or prevention of which can be effected or facilitated by inhibiting CRH binding protein, in a mammal, including a human, comprising administering to said mammal a CRH binding protein inhibiting amount of a compound of the formula I, or a pharmaceutically acceptable salt thereof.

This invention also relates to a pharmaceutical composition for treating or preventing a disorder or conditon, the treatment or prevention of which can be effected or facilitated by inhibiting CRH binding protein in a mammal, including a human, comprising a CRH binding protein inhibiting amount of a compound of the formula I, or a pharmaceutically acceptable salt thereof, and a pharmaceutically acceptable carrier.

This invention includes all optical isomers and other stereoisomers of compounds of the formula I. When such compounds contain one or more chiral centers, it is understood that the invention includes the racemic mixtures as well as all individual enantiomers and diastereomers of such compounds, and mixtures thereof.

DETAILED DESCRIPTION OF THE INVENTION

The following compounds having the formulas II, III, IV and V are useful as intermediates in the synthesis of compounds of the formula I.

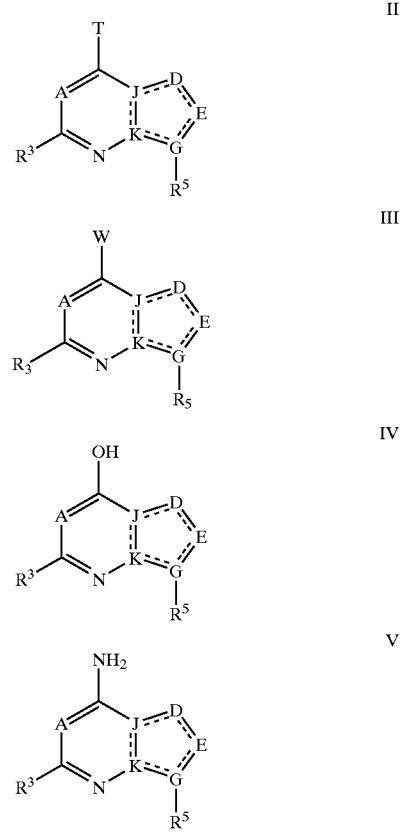

wherein T is chloro, bromo, iodo or —OSO$_2$CF$_3$; W is cyano, formyl, or —COO(C$_0$–C$_4$ alkyl) and A, J, K, D, E, G, R$^3$, and R$^5$ are as defined above with reference to formula I.

Compounds of the formula I may be prepared as described below. In the reaction schemes and discussion that follow, A, B, D, E, G, J, K, R$^3$, R$^5$ and structural formulae I, II, III, IV, and V are defined as above.

SCHEME 1

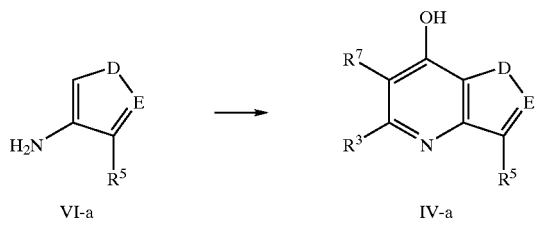

SCHEME 2
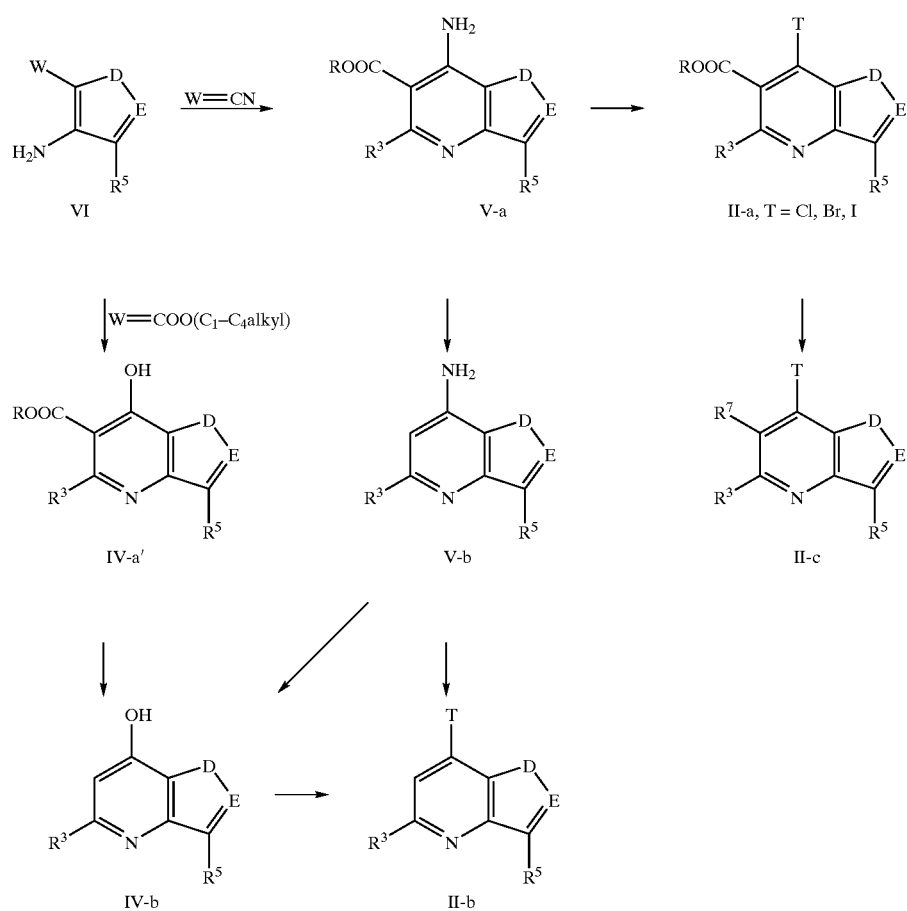
SCHEME 3
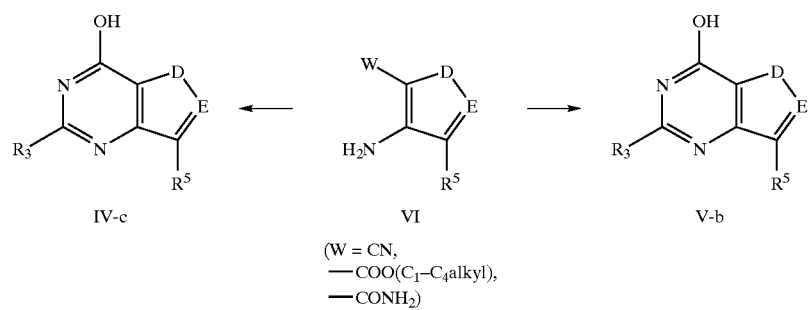
(W = CN,
—COO(C$_1$–C$_4$alkyl),
—CONH$_2$)
SCHEME 4
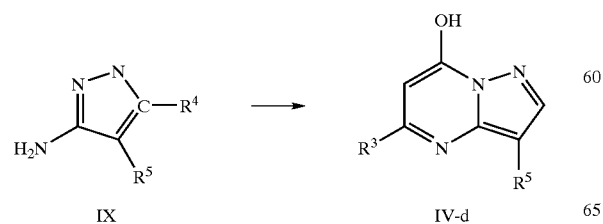
SCHEME 5
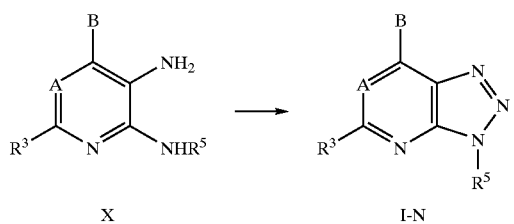

SCHEME 6
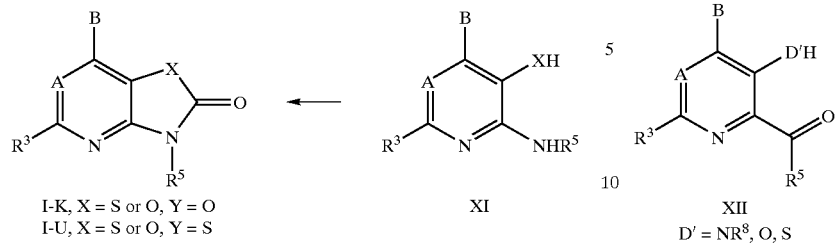
SCHEME 7
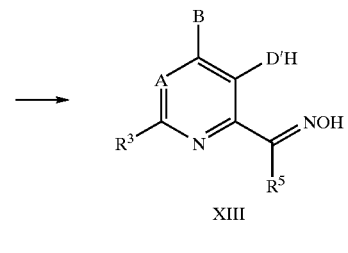
SCHEME 8
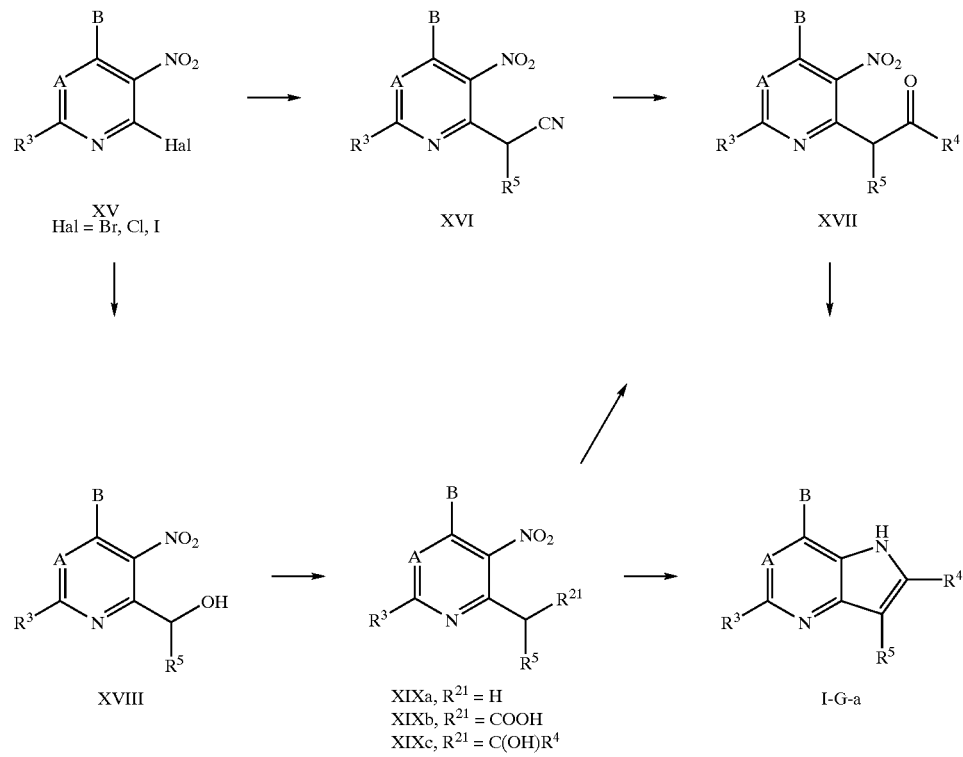

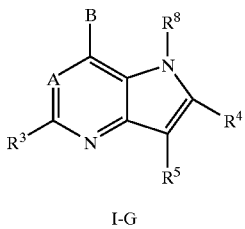

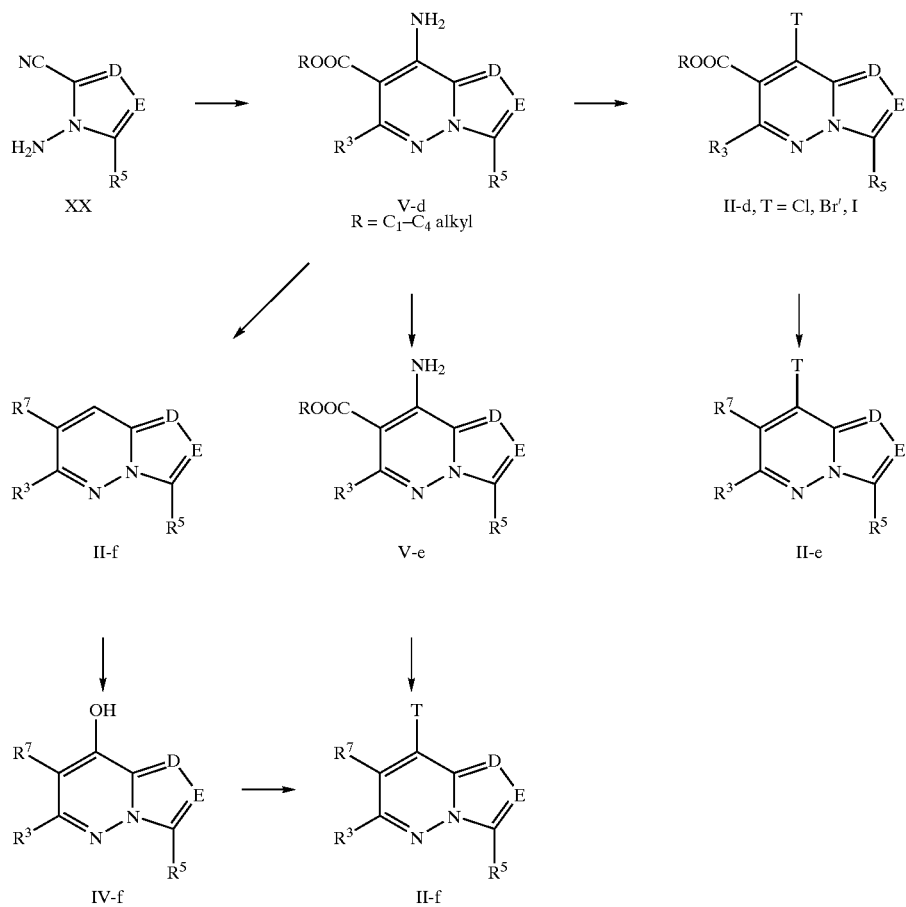

Compounds of the formula I wherein B is —NR$^1$R$^2$ or —NHCR$^1$R$^2$R$^{11}$ may be prepared by reacting a compound of the formula II wherein T is chloro, bromo, or iodo with a compound of the formula BH, in the presence of a base, with or without an organometallic compound such as Cu(I) X, wherein X is chloro, bromo or iodo, or an acid (such as p-TsOH (Ts=Tosyl) or another sterically hindered phenol) or an equivalent agent known to those of skill in the art. Suitable solvents for this reaction include DMSO, NMP, dimethylacetamide and THF. An excess of BH may be used as both the reagent and the base. Other bases such as potassium or sodium carbonate, a trialkylamine, a potassium or sodium (C$_1$–C$_4$ alkoxide) and sodium hydride may also be used. When R$^7$ is an electron withdrawing group such as —COO(C$_1$–C$_4$alkyl) or CN, the reaction generally is carried out at a temperature between about room temperature and about 100° C. When R$^7$ is a non-electron withdrawing group, the reaction temperature can generally range from about 50° C. to about 270° C. and the pressure can generally range from about 4 psi to about 300 psi. A pressure reactor may be used.

Alternatively, the compounds of formula I may be prepared by reacting a compound of the formula II wherein T is bromo or iodo with 1 equivalent or an excess of BH and a base such as sodium or potassium carbonate or a sodium or potassium (C$_1$–C$_4$ alkoxide), in the presence of a palladium (II) or a palladium (0) catalyst such as Pd(OAc)$_2$ or Pd(PPh$_3$)$_4$, together with a racemic or chiral phosphino agent such as 2,2-bis(diphenylphosphino)-1,1-binaphthyl (BINAP). Alternatively, premade Pd(II)(BINAP) may be used in an appropriate inert (i.e., inert with respect to the reaction at hand) solvent such as toluene, xylene, dioxane or sulfolane, at a temperature from about room temperature to about 180° C., preferably at about reflux temperature.

Compounds of the formula I wherein B is —OCR$^1$R$^2$R$^{11}$, —SCR$^1$R$^2$R$^{11}$, or —NHCR$^1$R$^2$R$^{11}$ may be prepared by reacting compounds in the formula II wherein T is chloro, bromo or iodo with a compound of the formula BH in the presence of a base which is capable of deprotonation of BH (e.g., sodium or potassium hydride, or an organometallic base such as sodium diisopropylamide, sodium bis (trimethylsilyl)amide, lithium diisopropylamide, lithium bis (trimethylsilyl)amide, a sodium $C_1$–$C_4$ alkoxide or n-butyllithium), in an inert organic solvent such as tetrahydrofuran, acetonitrile, dimethylsulfoxide, acetone, a $C_2$–$C_5$ alcohol, chloroform, benzene, xylene, toluene, N,N-dimethylformamide (DMF), methylene chloride, 1-methyl-2-pyrrolidinone or a mixture of two or more of the above solvents (e.g., DMSO and THF), at a temperature from about 0° C. to about 180° C., preferably from about 50° C. to about 180° C.

Compounds of the formula I wherein B is —$CR^1R^2R^{11}$, —$C(C=CR^2R^{12})R^1$, —$CR^2R^{11}NHR^1$, —$CR^2R^{11}OR^1$, —$CR^2R^{11}SR^1$, or —$C(O)R^2$ may be prepared from compounds of the formula III wherein W is cyano, formyl or carboxy, as described below.

Reacting compounds of formula III wherein W is cyano with a Grignard reagent containing the group $R^2$ in an inert solvent such as THF, glyme, ether or dioxane, will yield corresponding compounds of formula I wherein B is —$COR^2$. Further reaction of the compounds of formula I wherein B is $COR^2$ with a Grignard reagent containing $R^1$, using a solvent such as those referred to above, will yield the corresponding the compounds of formula I wherein B is —$CR^1R^2OH$. Reacting compounds of formula III wherein W is formyl with a Grignard reagent containing the group $R^2$, in an ethereal solvent such as those referred to above, will yield the corresponding compounds of formula I wherein B is —$CHR^2OH$.

Compounds of formula I wherein B is —$CR^1R^2R^{11}$ or —$C(C=CR^2R^{11})R^1$ may be prepared by conventional methods. Thus, reaction of a compound of the formula I wherein B is —$CR^1NR^2NOH$, (wherein $R^{1'}$ and $R^{2'}$ are defined as $R^1$ and $R^2$, respectively, except that $R^{1'}$ may not be $R^1$ and $R^{2'}$ may not be $R^2$), with an acid such as concentrated sulfuric acid in acetic acid, or a Burgess inner salt such as (carboxysulfamoyl)triethylammonium hydroxide methyl ester, will yield a compound of the formula I wherein B is —$C(=CR^2R^{11})R^1$. Hydrogenation of a compound of formula I wherein B is —$C(=CR^2R^{11})R^1$ using palladium on carbon (Pd/C) or a platinum dioxide catalyst in a ($C_1$–$C_4$)alkanol solvent will yield a compound of the formula I wherein B is —$CHR^1R^2$. Reaction of a compound of the formula I wherein B is —$CR^1R^2OH$ with diethylaminosulfur trifluoride or triphenylphosphine/carbon tetrachloride in an inert solvent such as carbon tetrachloride will afford a compound of the formula I wherein B is —$CR^1R^2F$ or —$CR^1R^2Cl$, respectively.

Reduction of a compound of formula I wherein B is —$COR^2$ with sodium borohydride, in an inert solvent such as a ($C_1$–$C_4$)alkanol, will yield a compound of the formula I wherein B is —$CHR^2OH$. Alkylation of a compound of the formula I wherein B is —$CHR^2OH$ with an alkyl halide (such as alkyl iodide) in the presence of a base such as sodium hydride (NaH) at room temperature, in an inert solvent such as toluene, THF, dioxane or ether, will yield the corresponding compound of the formula I wherein B is —$CHR^2OR^1$.

Compounds of the formula I wherein B is —$CR^2R^{10}NHR^1$ may be prepared by conventional methods such as reductive amination of the corresponding compounds of the formula I wherein B is —$C(O)R^2$ with an appropriate amine and reducing agent (such as sodium cyanoborohydride, sodium triacetoxyborohydride, or lithium aluminum tetrahydride) in an appropriate inert solvent such as a $C_1$–$C_4$ alkanol or acetic acid.

Conversion of compounds in formula I wherein B is —$C(O)R^2$ into compounds in formula I wherein B is —$C(S)R^2$ can be accomplished using standard methods well known in the art (e.g., using Lawesson's Reagent or diphosphorus pentasulfide ($P_2S_5$)). Reduction of compounds of the formula I wherein B is —$C(S)R^2$ with a reducing agent such as sodium borohydride or lithium aluminum tetrahydride gives the corresponding compounds of the formula I wherein B is —$CHR^2SH$. Alkylation of compounds of the formula I wherein B is —$CHR^2SH$ with alkyl halide (such as alkyl iodide) in the presence of a base such as sodium hydride in an inert solvent such as THF, DMF or toluene at about room temperature will afford the corresponding compounds of the formula I wherein B is —$CHR^2SR^1$.

Compounds in formula II may be prepared from compounds of the formula IV or V as described below.

Compounds of formula II wherein T is chloro, bromo or iodo can be prepared by reacting compounds of the formula IV with from one equivalent to an excess of $POT_3$ (wherein T is chloro, bromo or iodo) in the presence or absence of a di($C_1$–$C_4$ alkyl)aniline, preferably diethylaniline, with or without a solvent (such as dichloroethane, DMF, dimethylsulfoxide (DMSO) or acetamide), at a temperature from about room temperature to about 180° C., preferably from about 100° C. to about 150° C. Alternatively, compounds of formula II wherein T is chloro, bromo or iodo can be prepared by reacting the corresponding compounds of formula II wherein T is —O—$SO_2CF_3$ with a sodium or potassium halide, in an appropriate inert solvent such as THF, sulfolane, DMSO, DMF or acetonitrile, at a temperature from about 60° C. to about 180° C. Compounds of formula II wherein T is —$OSO_2CF_3$ can be prepared by reacting compounds of formula IV with $Tf_2O$ in the presence of a base such as triethylamine or pyridine, in an appropriate inert solvent such as THF, methylene chloride, dioxane, ether or toluene, at an temperature from about 0° C. to about 50° C., preferably from about 0° C. to about room temperature.

Alternatively, compounds of formula II wherein T is chloro, bromo or iodo may be prepared by reacting compounds of formula V with a ($C_1$–$C_7$ alkyl)-nitrite and Cu(I)$T_2$ (wherein T is chloro, bromo or iodo) in an appropriate inert solvent such as acetonitrile, acetone, methylene chloride, THF, dioxane, benzene, toluene, dichloroethane, DMF, DMSO or N-methylpyrrolidinone (NMP) at a temperature from about room temperature to about 150° C., preferably from about 40° C. to about 100° C.

Compounds of the formula IV may be prepared by reacting the appropriate compounds of formula V with sodium nitrite ($NaNO_2$) in an aqueous acid such as sulfuric acid, acetic acid or phosporic acid, with or without an organic solvent, preferably in acetonitrite ($CH_3CN$) or acetone.

Compounds of formula III wherein W is cyano can be prepared by reacting the corresponding compounds of formula II wherein T is chloro, bromo or iodo with potassium cyanide, copper cyanide, sodium cyanide or a di($C_1$–$C_4$alkyl)aluminum cyanide in an appropriate inert solvent such as dimethylsulfoxide, DMF, toluene or xylene, at temperature from about room temperature to about 180° C., preferably from about 60° C. to about 150° C., with or without Pd(II)OAc or Pd(0)(PPh$_3$)$_4$.

Compounds of formula III wherein W is —CHO or —COOH may be prepared by reacting compounds in formula II wherein T is bromo or iodo with an organolithium reagent such as t-BuLi, s-BuLi, or n-BuLi in an appropriate inert solvent such as THF, dioxane, ether, benzene or methylene chloride, at temperature from about −120° C. to about room temperature, preferably from about −110° C. to about −60° C., followed by quenching with an appropriate electrophile such as DMF or $CO_2$ (gas or dry ice), to give compounds of formula III wherein W is —CHO and —COOH, respectively.

It is understood that the general organic chemistry knowledge can be applied to change the steps of the reaction sequences described herein depending on the feasibility of the reaction. For example, a protecting group may be used at any stage of the various syntheses described above at which it is workable, or an ester group may be reduced to the corresponding $C_1$–$C_4$ alkyl group at any convenient stage. Compounds of formulas I–XVIII, wherein $R^3$ is chloro, bromo, —COO($C_1$–$C_4$ alkyl) or —COOH, can be converted to the corresponding compounds wherein $R^3$ is ($C_1$–$C_4$ alkyl), —O($C_1$–$C_4$ alkyl), fluoro, —S($C_1$–$C_4$ alkyl) at any convenient stage, as appropriate, in the syntheses referred to above using methods described in the literature. Compounds of formula I–XVIII, wherein $R^3$ is —O($C_1$–$C_4$ alkyl) or —S($C_1$–$C_4$ alkyl) can be prepared by reacting the corresponding compounds wherein $R^3$ is chloro, bromo or iodo, with a nucleophile such as a $C_1$–$C_4$ alkanol or a $C_1$–$C_4$ alkanethiol, in the presence of an organic or inorganic base. Suitable bases for such a reaction include sodium and sodium hydride. Compounds of formulas I–XVIII wherein $R^3$ is fluoro can be prepared by reacting the corresponding compounds wherein $R^3$ is chloro with tetrabutylammonium fluoride in a suitable inert solvent such as DMSO, methylene chloride, or tetrahydrofuran. Tetrahydrofuran is preferred.

Reduction of an ester or carboxylic acid using lithium aluminum tetrahydride/aluminum trichloride ($LiAlH_4$/$AlCl_3$) in an appropriate inert solvent such as THF, ether, or dioxane, at temperature from about 100° C. to about room temperature, will afford the corresponding compound wherein $R^3$ is $CH_3$. Conversion of compounds wherein B is —COOH to the corresponding compounds wherein B is —CO($C_1$–$C_3$ alkyl) may be accomplished using standard alkylation methods well known in art. Reduction of compounds wherein B is —CO($C_1$–$C_3$ alkyl) using standard methods well known in the art will afford the corresponding compounds wherein $R^3$ is one of various ($C_1$–$C_4$ alkyl) derivatives.

Compounds of the formula IV-a wherein A is $CR^7$ and G, J, and K are carbon may be prepared by heating compounds of formula VI-a with an appropriate compound of the formula $R^3C(O)CR^7COO(C_1$–$C_4$ alkyl) under acid or Lewis acid conditions with or without a solvent, as shown in Scheme 1. Examples of such reaction conditions are: a) heating in polyphosphoric acid; b) heating in toluene, benzene or xylene in the presence of acid catalyst (such as p-TsOH, sulfuric acid or HCl(g)) using a Dean-Stark trap; or c) heating in an appropriate solvent such as dichloroethane, diphenylether ($Ph_2O$) or Dowtherm A in the presence of a Lewis acid such as $SnCl_4$, $ZnCl_2$/HCl or $AlCl_3$.

Compounds of formula VI-a may be prepared using methods described in the scientific literature. (See *Gazz. Chim. Ital.*; 111, p167–172(1981); *Chem. Pharm. Bull.*; 24, 3001–3010 (1976); *J. Org. Chem.*, 38, 1777–1780 (1973); *Chem. Abstr.* 68, 68982f (1968); *Aust. J. Chem.*; 22, 563–572(1969); *J. Chem. Soc. Perkin Trans.*2, p1954, p1957 (1972); *J. Heterocycl. Chem.*; FR, 19, 443–445 (1982); *J. Heterocycl. Chem.*, 22, 1496–1502 (1985); *Tetrahedron*, 47, 4639–4644 (1991); *J. Heterocycl. Chem.*, 28, 2053–2055 (1991); *J. Heterocycl. Chem.*, 29, 251–153 (1992).

Compounds of formula V-a and IV-a', wherein R is $C_1$–$C_4$alkyl can be prepared by heating compounds of formula VI wherein W is —CN and —COO($C_1$–$C_4$ alkyl), respectively, with an appropriate $R^3C(O)CH_2COO(C_1$–$C_4$ alkyl) in the presence of a Lewis acid such as $SnCl_4$, $AlCl_3$, $TiCl_3$ or $ZnCl_2$, in a inert solvent such as dichloroethane, at about the reflux temperature, as shown in Scheme 2. Base hydrolysis of a compound of the formula V-a or IV-a$^\&$ with sodium hydroxide in $H_2O$/($C_1$–$C_4$ alcohol) at reflux, or with lithium hydroxide in water/THF or water/dioxane at temperature from about room temperature to about the reflux temperature, followed by decarboxylation by heating in a oil bath at a temperature from about 140–180° C. will give a compound of formula V-b or IV-b, respectively. Compounds of the formulas V-a and IV-a$^\&$ may be converted into compounds of the formula II-a, and compounds of the formulas V-b and IV-b may be converted into compounds of the formula II-b by the procedures described above. The conversion of compounds of the formula II-a into those of the formula II-c can be accomplished using procedures analogous to those described above for converting compounds wherein $R^3$ is —COO($C_1$–$C_4$ alkyl) into those wherein $R^3$ is $C_1$–$C_4$ alkyl.

Compounds of formula VI may be prepared using methods described in the literature. (See *Liebigs Ann Chem.*, 1534–1546, 1979; *Gazz. Chim. Ital.*, 97, 25–33, 1967; *Gazz. Chim. Ital.*, 120, 725–730, 1990; *Eur. J. Med. Chem. Chim. Ther.*, 26, 143–158, 1991; *J. Heterocycl. Che., Fr.* 19, 443–445, 1982; *J. Heterocycl. Chem.*, 22, 1496–1502, 1985; *J. Heterocycl. Chem.*, 31, 305–312, 1994; *J. Heterocycl. Chem.*, 24, 243–245, 1987; *J. Org. Chem.* 57, 3713–3716, 1992; *Liebigs Ann Chem.*, 1702–1710, 1984; *Chem. Pharm. Bull.*, 34, 701–702, 1986; *Pharmazie*, 48, 849–853, 1993; *Bull. Soc. Chim. Belg.*, 103, 181–184, 1994; and *Indian. J. Chem. Sect. B*, 33, 436–440,1994).

Compounds of formula IV-c wherein A is N and G, J, and K are carbon may be prepared, as shown in Scheme 3, by reacting compounds of formula VI with ($R^3CO)_2O$, $R^3COOH$ or $R^3CO(OC_1$–$C_2$ alkyl)$_3$, in acetic acid or an appropriate inert organic solvent such as toluene, dioxane, acetonitrile, methylene chloride or chloroform, at a temperature from about 25° C. to about 150° C., preferably at about the reflux temperature, followed by heating in 85% phosphoric acid or an aqueous acid such as acetic acid, hydrochloric acid or sulfuric acid, preferably in 50–85% phosphoric acid. Compounds of formula V-b may be prepared, as shown in Scheme 3, by heating the corresponding compounds of formula VI with excess of the appropriate compound of the formula $R^3CONH_2$.

Compounds of formula IV-d may be prepared, as shown in Scheme 4, by reacting compounds of formula IX with an appropriate reagent having the formula $R^3C(O)CHR^7COO$ ($C_1$–$C_4$alkyl) in an $R^3COOH$ solvent at temperature from about 60° C. to about 180° C., preferably at about the reflux temperature.

Compounds of formula I-N may be prepared, as shown in Scheme 5, by reacting the corresponding compounds of formula X with a ($C_1$–$C_7$ alkyl)nitrite, with or without $CuBr_2$, $CuCl_2$, or $CuI_2$, in an appropriate inert solvent such as acetonitrile, acetone, methylene chloride, chloroform, benzene or toluene, preferably acetonitrile at a temperature from about 25° C. to about 150° C., preferably from about 60° C. to 100° C.

Compounds of formula I-L and I-M may be prepared, as shown in Scheme 6, by reacting compounds of formula XI wherein X is S or O with a compound of the formula $R^4CHO$ or $R^4CH(OC_1$–$C_2$ alkyl)$_2$ and an acid catalyst such as p-TsOH, HCl, HBr, $H_2SO_4$, or HCl, in toluene, xylene or benzene, preferably toluene, with from one to ten equivalents of water, at temperature from about 70° C. to about 160° C., using a Dean-Stark trap or in the presence of anhydrous sodium sulfate.

Compounds of formula I-K and I-U may be prepared by reacting the corresponding compounds of formula Xi with triphosgene and thiophosgene, respectively, and a base such as triethylamine or pyridine in an appropriate inert solvent such as methylene chloride, THF, dioxane, ether, benzene or chloroform, preferably methylene chloride or dry THF, at temperature from about 0° C. to about 25° C.

Compounds of formula I-V, I-W, and I-X may be prepared, as illustrated in Scheme 7, starting from compounds of formula XII. Compounds of formula XIII may be prepared by reacting the corresponding compounds of formula XII with hydroxylamine in acidic (e.g., in trifluoroacetic acid) or basic (e.g., in NaOAc or NaOH and hydroxylamine hydrochloride in a $C_1$–$C_4$ alcohol/water mixture) conditions at temperatures from about 25° C. to about 150° C., preferably at about the reflux temperature. Compounds of formula XIV can be prepared by heating the corresponding compounds of formula XIII in acetic anhydride, trifluoroacetic anhydride or $Tf_2O$, with or without a solvent such as acetic acid or methylene chloride, in the presence of an appropriate amine base such as triethylamine or pyridine. Compounds of formula I-V, I-W and I-X may be prepared by heating the corresponding compounds of formula XIV and pyridine in an inert solvent such as DMF, DMSO, NMP, sulfolane or acetamide at a temperature from about 80° C. to about 180° C.

Compounds of formula I-G may be prepared, as illustrated in Scheme 8, by reducing the corresponding compounds of formula XVII. This reduction can be performed using standard methods known in literature for reduction of a nitro group to an amino group. Such methods include hydrogenation or reduction by iron in acetic acid. Cyclization may occur upon reduction or heating in an appropriate solvent such as a $C_1$–$C_4$ alcohol, acetonitrile, toluene, THF, methylene chloride or acetic acid.

The conversion of compounds of formula XVI into those of formula XVII can be accomplished using methods analogous to those described above for the conversion of compounds of formula V wherein W is cyano into compounds of formula I wherein B is a group having a carbon atom directly attached to the bicyclic ring. The best method for conversion of a cyano group to a —COOH group is acid hydrolysis, for example, heating the cyano compound in 50–85% phosphoric acid or 50–90% acetic acid, preferably phosphoric acid. The best method for converting a cyano group into a —CO($C_1$–$C_4$ alkyl) is reacting the cyano compound with a Grignard reagent at a temperature from about 0° C. to about 25° C. in ether, THF or dioxane. The best method for converting a cyano group into a —CHO group is a diisobutylaluminum hydride reduction in THF, dioxane, or ether at a temperature from about –78° C. to about 25° C., preferably from about –78° C. to about –40° C.

Compounds of the formula XVI may be prepared by reacting compounds of formula XV, wherein Hal is chloro, bromo or iodo, with a sodium, potassium, or lithium salt of $R^5CH_2CN$ in an appropriate inert solvent such as toluene, benzene, a $C_1$–$C_5$ alcohol, THF, DMSO, dioxane, or pyridine, with or without a Pd(II) or Pd(0) catalyst, at a temperature from about –78° C. to about 130° C.

Alternatively, compounds of formula XVII may be prepared by subjecting compounds of the formula XV to halogen-metal exchange (e.g., using an organo lithium agent such as tBuLi, s-BuLi or BuLi at –78° C. in ether, THF, or dioxane), followed by quenching with an electorphile such as $R^5CHO$, to give compounds of formula XVIII. Compounds of formula XIX-a may be prepared by reacting the corresponding compounds of formula XVIII with thionyl chloride, followed by reduction. Reacting compounds of formula XIX-a with a base (such as organolithium agent (e.g., lithium diisopropylamide or BuLi), followed by quenching with an electrophile (such as carbon dioxide) will yield the corresponding compounds of formula XIX-b wherein $R^{21}$ is —COOH. Compounds of formula XIX-c wherein $R^{21}$ is —C(OH)$R^4$ may be prepared in a similar fashion by quenching the appropriate compound of formula XIX-a with an electrophile of the formula $C_1$–$C_3$ alkyl-CHO. Compounds of formula XVII can be prepared by reacting compounds of formula XIX-c with PCC (pyridinium chlorochromate) using standard PCC oxidation methods that are well known in the art.

Compounds of formula II-d, II-e and II-f, wherein T is chloro, bromo or iodo and D, E, $R^3$, $R^5$ and $R^7$ are as defined to those in formula I may be prepared, as shown in Scheme 9, by methods analogous to those described in Scheme 2. Alternatively, Compounds of formula II-d to II-f may be prepared using procedures analogous to those described in the literature (See: Pharm. Bull, 5, 229–231, 1957; *Monatsh Chem*, 100, 671–678, 1969; *J. Heterocycl. Chem.*, 3, 218–220, 1966, *Chem. Pharm. Bull,.* 23, 2891–2895, 1975; *J. Heterocycl. Chem.*, 8, 1–6, 1971; *Justus Liebigs Ann. Chem*, 735, 35–44, 1970; *Tetrahedron Lett*, 1479, 1968; and *Chem. Abstr.*, 1939, 4988.)

The acid addition salts of compounds of the formula can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The compounds of formula I and their pharmaceutically acceptable salts (hereinafter referred to, collectively, as "the active compounds of this invention") may be administered alone or in combination with pharmaceutically acceptable carriers, in either single or multiple doses. Suitable pharmaceutical carriers include inert solid diluents or fillers, sterile aqueous solutions, oils (e.g., sesame oil, peanut oil) and various organic solvents. The pharmaceutical compositions formed by combining the novel compounds of formula I and pharmaceutically acceptable carriers can then be readily administered in a variety of dosage forms such as tablets, oil gel, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules.

Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for the active compounds of this invention will depend on the intended route of administration and factors such as the age and weight of the patient, as generally known to a physician. The dosages will also depend on the particular illness to be treated. For instance, the daily dosage for stress-induced illnesses, inflammatory disorders, Alzheimer's disease, gastro-intestinal diseases, anorexia nervosa, hemorrhagic stress and drug and alcohol withdrawal symptoms will generally range from about 0.1 to about 50 mg/kg body weight of the patient to be treated.

Methods that may be used to determine the CRF antagonist activity of the active compounds of this invention and their pharmaceutically acceptable salts are described in *Endocrinology*, 116, 1653–1659 (1985) and *Peptides*, 10, 179–188 (1985). The binding activities for compounds of the formula I, expressed as $IC_{50}$ values, generally range from about 0.5 nanomolar to about 10 micromolar. Methods that can be used to determine the CRF binding protein inhibiting activity of compounds of the formula I are described in *Brain Research*, (1997), 745 (1,2),248–255.

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochloroform (CDCl$_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

The following abbreviations are used in the Examples: Ph=phenyl; iPr=isopropyl.

EXAMPLE 1

7-(1-Ethyl-propoxy)-5-methyl-3-(2,4,6-trimethyl-phenyl)-pyrazolo[1,5-a]pyrimidine A solution of 3-pentanol (140 mg, 1.5 mmol) in 1 ml of dry THF was treated with 60% sodium hydride in oil (28 mg, 0.7 mmol) and stirred at room temperature for 10 min. A solution of 7-chloro-5-methyl-3-(2,4,6-trimethyl-phenyl)-pyrazolo[1,5-a]pyrimidine (75 mg, 0.262 mmol) in 1 ml of dry THF was added and the resulting mixture was heated at reflux for 5 hours. The mixture was quenched with water and extracted with ethyl acetate. The organic layer was washed with brine, dried and concentrated to give the crude material. The residue was purified through silica gel column chromatography using 3:7 chcloroform:hexane as eluent to give 75 mg (88%) of the title compound. $^1$H NMR (CDCl$_3$) ä 7.97(s, 1H), 6.97(s, 2H), 6.03(s, 1H), 4.56(m, 1H), 2.53(s, 3H), 2.32(s, 3H), 2.13(s, 6H), 2.10(m, 4H), 1.09(t, 6H) ppm.

EXAMPLE 2

[2,5-Dimethyl-3-(2,4,6-trimethyl-phenyl)-pyrazolo[1,5-a]pyrimidin-7-yl]-(1-ethyl-propyl)-amine A mixture of 7-Chloro-2,5-dimethyl-3-(2,4,6-trimethyl-phenyl)-pyrazolo[1,5-a]pyrimidine (60 mg, 0.2 mmol) and 1-ethylpropylamine (4 ml) in 1 ml of N-methylpyrrolidinone was heated at 125° C. oil bath for 15 hrs. The mixture was quenched with water and extracted with ethyl acetate. The organic layer was dried and concentrated and purified through silica gel column chromatography using 20% ethyl acetate in hexane as eluent to give 35 mg of the title compound as a yellow solid. $^1$H NMR (CDCl$_3$) ä 6.96(s, 2H), 6.00(d, 1H), 5.77(s, 1)H, 3.47 (m, 1H), 2.43(s, 3H), 2.32(s, 3H), 2.22(s, 3H), 2.05(s, 6H), 1.5–1.9(m, 4H), 1.04(t, 6H) ppm.

EXAMPLE 3

(1-Ethyl-propyl)-[5-methyl-3-(2,4,6-trimethyl-phenyl)-pyrazolo[1,5-a]pyrimidin-7-yl]-amine A mixture of 7-chloro-5-methyl-3-(2,4,6-trimethyl-phenyl)-pyrazolo[1,5-a]pyrimidine (190 mg, 0.63 mmol) and 1-ethylpropylamine (4 ml) in 1 ml of N-methylpyrrolidinone was heated at 125° C. oil bath for 15 hours. The mixture was quenched with water and extracted with ethyl acetate. The organic layer was dried and concentrated and purified through silica gel column chromatography using chloroform to 2% methanol in chloroform as eluent to give 195 mg (87%) of the title compound as a green solid. $^1$H NMR (CDCl$_3$) ä 7.87(s, 1H), 6.97(s, 2H), 6.12(d, 1H), 5.85(s, 1H), 3.52(m, 1H), 2.48(s, 3H), 2.09(s, 3H), 2.16(s, 6H), 1.6–1.9(m, 4H), 1.05(t, 6H)ppm.

EXAMPLE 4

7-(1-Ethyl-propoxy)-2,5-dimethyl-3-(2,4,6-trimethyl-phenyl)-pyrazolo[1,5-a]pyrimidine To a suspension of 60% Sodium hydride in oil (160 mg) in 4 ml of DMSO was added 3-pentanol (853 mg), and then 7-chloro-2,5-dimethyl-3-(2,4,6-trimethyl-phenyl)-pyrazolo[1,5-a]pyrimidine (580 mg) at room temperature. The mixture was heated at 88° C. overnight. The mixture was quenched with water and extracted with ethyl acetate. The organic layer was dried and concentrated and purified through silica gel column chromatography using 10% hexane in chloroform as eluent to give the title compound as an orange oil. $^1$H NMR (CDCl$_3$) ä 6.96(s, 2H), 5.95(s, 1H), 4.52(m, 1H), 2.48(s, 3H), 2.33(s, 3H), 2.27(s, 3H), 2.03(s, 6H), 1.75–2.00(m, 4H), 1.08(t, 6H)ppm.

EXAMPLE 5

[2,5-Dimethyl-3-(2,4,6-trimethyl-phenyl)-pyrazolo[1,5-a]pyrimidin-7-yl]-ethyl-propyl-amine A mixture of 7-chloro-5-methyl-3-(2,4,6-trimethyl-phenyl)-pyrazolo[1,5-a]pyrimidine (200 mg, 0.66 mmol) and N-propylethylamine (2 ml) in 1 ml of N-methylpyrrolidinone was heated at 135° C. oil bath for 4 hours. The mixture was quenched with water and extracted with ethyl acetate. The organic layer was dried and concentrated and purified through silica gel column chromatography using hexane to 10% ethyl acetate in hexane as eluent to give 150 mg of the title compound as a clear green oil. $^1$H NMR (CDCl$_3$) ä 6.95(s, 2H), 5.80(s, 1H), 3.85(q, 2H), 3.67(dd, 2H), 2.41(s, 3H), 2.32(s, 3H), 2.21(s, 3H), 2.03(s, 6H), 1.76(m, 2H), 1.29(t, 3H), 0.98(t, 3H) ppm.

EXAMPLE 6

[6-Bromo-5-bromomethyl-3-(2,4,6-trimethyl-phenyl)-3H-[1,2,3]triazolo[4,5-b]pyridin-7-yl]-(1-ethyl-propyl)-amine To a solution of butyl nitrite (119 mg, 1.15 mmol) and CuBr2 (205 mg, 0.919 mmol) in 16 ml of acetonitrile was added N4-(1-ethyl-propyl)-6-methyl-N2-(2,4,6-trimethyl-phenyl)-pyridine-2,3,4-triamine (250 mg, 0.766 mmol). The resulting mixture was heated at 65° C. for 1.5 hrs. The mixture was cooled to room temperature and 2N HCl (16 ml) was added. The mixture was neutralized with 2N NaOH and extracted with ethyl acetate. The organic layer was washed with brine, dried and concentrated to give a brown oil. The oil residue was purified through silica gel column chromatography using 1:1 hexane:ethyl acetate as eluent to give 61 mg of [6-bromo-5-bromomethyl-3-(2,4,6-trimethyl-phenyl)-3H-[1,2,3]triazolo[4,5-b]pyridin-7-yl]-(1-ethyl-propyl)-amine as white crystals. Mp 123–125° C. $^1$H NMR (CDCl$_3$) ä 7.06(s, 2H), 5.53(d, 1H), 5.22(m, 1H), 4.67(s, 2H), 2.39(s, 3H), 1.96(s, 6H), 1.6–1.9(m, 4H), 1.06(t, 6H)ppm and 103 mg of [6-bromo-5-methyl-3-(2,4,6-trimethyl-phenyl)-3H-[1,2,3]triazolo[4,5-b]pyridin-7-yl]-(1-ethyl-propyl)-amine as white solid. Mp 115–117° C. $^1$H NMR (CDCl$_3$) ä 7.04(s, 2H), 5.36(d, 1H), 5.21(m, 1H), 2.64(s, 3H), 2.38(s, 3H), 1.95(s, 6H), 1.6–1.9(m, 4H), 1.05(t, 6H)ppm.

EXAMPLE 7

(1-Ethyl-propyl)-[5-methyl-3-(2,4,6-trimethyl-phenyl)-3H-[1,2,3]triazolo[4,5-b]pyridin-7-yl]-amine A mixture of butyl nitrite (119 mg, 1.15 mmol) and N4-(1-ethyl-propyl)-6-methyl-N2-(2,4,6-trimethyl-phenyl)-pyridine-2,3,4-triamine (250 mg, 0.766 mmol) in anhydrous acetonitrile (16 ml) was heated at 65° C. for 2 hours. The mixture was cooled to room temperature and 2N HCl (16 ml) was added. The mixture was neutralized with 2N NaOH and extracted with ethyl acetate. The organic layer was washed with brine, dried and concentrated to give 250 mg of the crude product as a brown oil. The oil residue was purified through silica gel column using chloroform as eluent to give 201 mg of the title compound as golden yellow solid. Mp 131–133° C. $^1$H NMR (CDCl$_3$) ä 7.022(s, 2H), 6.20(s, 1H), 5.44(d, 1H), 3.65(m, 1H), 2.50(s, 3H), 2.36(s, 3H), 1.96(s, 6H), 1.5–1.8(m, 4H), 1.03(t, 6H)ppm.

EXAMPLE 8

[6-Bromo-5-methyl-3-(2,4,6-trimethyl-phenyl)-3H-[1,2,3]triazolo[4,5-b]pyridin-7-yl]-(1-ethyl-propyl)-methyl-amine To a solution of [6-bromo-5-methyl-3-(2,4,6-trimethyl-phenyl)-3H-[1,2,3]triazolo[4,5-b]pyridin-7-yl]-(1-ethyl-propyl)-amine (50 mg, 0.12 mmol) in dry THF )1.5 ml) was added 2.5 M n-BuLi in hexane (0.14 ml) at −78° C. After stirring at −78° C. for 10 min, 0.5 ml of methyl iodide was added at that temperature then allowed to warmed to room temperature and stirred for 15 min for 2 hours. The mixture was quenched with water and extracted with ethyl acetate. The organic layer was washed with brine, dried and concentrated to give 46 mg of brown oil. The residue was purified through silica gel coliumn chromatography using 1:1 chloroform:hexane as eluent to give the title compound as a golden oil. $^1$H NMR (CDCl$_3$) ä 7.04(s, 2H), 4.35(m, 1H), 3.32(s, 3H), 2.70(s, 3H), 2.38(s, 3H), 1.94(s, 6H), 1.7–2.0(m, 4H), 1.01(t, 6H)ppm.

EXAMPLE 9

7-(1-Ethyl-propoxy)-5-methyl-3-(2,4,6-trimethyl-phenyl)-3H-[1,2,3]triazolo[4,5-b]pyridine A mixture of 4-(1-Ethyl-propoxy)-6-methyl-N2-(2,4,6-trimethyl-phenyl)-pyridine-2,3-diamine (50 mg, 0.153 mmol) and butyl nitrite (24 mg, 0.229 mmol) in 4 ml acetonitrile was heated at 65° C. for 2 hours. An additional 0.13 ml of butyl nitrite was added and the resulting mixture was heated at 65° C. for 2 hours. The mixture was quenched with water and extracted with ethyl acetate. The organic layer was dried and concentrated to give 58 mg of brown oil. The oil was purified through silica gel column chromatography using 5% ethyl acetate in hexane as eluent to give 46 mg (88%) of the title compound as a light yellow oil. $^1$H NMR (CDCl$_3$) ä 7.04(s, 2H), 6.60(s, 1H), 5.26(m, 1H), 2.57(s, 3H), 2.38(s, 3H), 1.94(s, 6H), 1.8–2.0(m, 4H), 1.07(t, 6H) ppm.

EXAMPLE 10

4-(1-Ethyl-propoxy)-2,5-dimethyl-7-(2,4,6-trimethyl-phenyl)-5H-pyrrolo[3,2-d]py-rimidine To a solution of 3-pentanol (0.09 ml, 0.883 mmol) in dry THF was added 60% NaH in oil (20 mg, 0.500 mmol) and stirred for 5 min. A solution of 4-chloro-2,5-dimethyl-7-(2,4,6-trimethyl-phenyl)-5H-pyrrolo[3,2-d]pyrimidine (50 mg, 0.166 mmol) in dry THF was added to the reaction mixture and the resulting mixture was heated at reflux for 2 hr. The mixture was quenched with water, extracted with ethyl acetate. The organic layer was washed with brine, separated, dried and concentrated to dryness to give the title compound as a white solid. $^1$H NMR (CDCl$_3$) ä 6.92(s, 3H), 5.43(m, 1H), 4.02(s, 3H), 2.56(s, 3H), 2.29(s, 3H), 2.08(s, 6H), 1.80(m, 4H), 0.99(t, 6H).

The title compounds of Examples 11–14 were prepared by the method analogous to that described in Example 10 starting from of 4-chloro-2-methyl-5-substituted-7-(substituted-phenyl)-5H-pyrrolo[3,2-d]pyrimidine or 7-chloro-5-methyl-1-substituted-3-(substituted-phenyl)-1H-pyrrolo[3,2-b]pyridine and an appropriate alcohol or thiol and a base.

EXAMPLE 11

(+)-2,5-Dimethyl-4-(tetrahydro-furan-3-yloxy)-7-(2,4,6-trimethyl-phenyl)-5H-pyrrolo[3,2-d]pyrimidine $^1$H NMR (CDCl$_3$) ä 6.95(s, 1H), 6.92(s, 2H), 5.88(m, 1H), 3.9–4.08(m, 4H), 4.01(s, 3H), 2.56(s, 3H), 2.29(s, 3H), 2.2–2.4(m, 2H), 2.07(s, 6H) ppm.

EXAMPLE 12

2,5-Dimethyl-4-(S)-(tetrahydro-furan-3-yloxy)-7-(2,4,6-trimethyl-phenyl)-5H-pyrrolo[3,2-d]pyrimidine $^1$H NMR (CDCl$_3$) ä 6.95(s, 1H), 6.92(s, 2H), 5.88(m, 1H), 3.9–4.08(m, 4H), 4.01(s, 3H), 2.56(s, 3H), 2.29(s, 3H), 2.2–2.4(m, 2H), 2.07(s, 6H) ppm.

EXAMPLE 13

2,5-Dimethyl-4-(1-propyl-butoxy)-7-(2,4,6-trimethyl-phenyl)-5H-pyrrolo[3,2-d]pyrimidine $^1$H NMR (CDCl$_3$) ä 6.93(s, 2H), 6.92(s, 1H), 5.58(m, 1H), 4.02(s, 3H), 2.56(s, 3H), 2.29(s, 3H), 2.09(s, 6H), 1.6–1.8 (m, 4H), 1.4–1.6(m, 4H), 0.96(t, 6H)ppm.

EXAMPLE 14

4-sec-Butylsulfanyl-2,5-dimethyl-7-(2,4,6-trimethyl-phenyl)-5H-pyrrolo[3,2-d]pyrimidine $^1$H NMR (CDCl$_3$) ä 6.97(s, 1H), 6.94(s, 2H), 4.34(m, 1H), 4.13(s, 3H), 2.63(s, 3H), 2.30(s, 3H), 2.07(s, 6H), 1.7–1.9 (m, 2H), 1.48(d, 3H), 1.09(t, 3H) ppm.

The title compounds of Examples 15–18 were prepared using the following procedure.

PROCEDURE FOR EXAMPLES 15–18

A mixture of 4-chloro-2-methyl-5-substituted-7-(substituted-phenyl)-5H-pyrrolo[3,2-d]pyrimidine or 7-bromo-1,5-dimethyl-3-(2,4,6-trimethyl-phenyl)-1H-pyrrolo[3,2-b]pyridine-6-carboxylic acid methyl ester (1 mmol) and an appropriate amine in DMSO (2 ml) was heated in 130° C. oil bath until all the starting material was consumed. The mixture was quenched with water and extracted with ethyl acetate. The organic layer was dried and concentrated to dryness to give the corresponding 4-alkylamino-2-methyl-5-substituted-7-(substituted-phenyl)-5H-pyrrolo[3,2-d]pyrimidine or 7-alkylamino-1,5-dimethyl-3-(2,4,6-trimethyl-phenyl)-1H-pyrrolo[3,2-b]pyridine-6-carboxylic acid methyl ester derivative. Silica gel column chromatography may be used for purification.

EXAMPLE 15

[2,5-Dimethyl-7-(2,4,6-trimethyl-phenyl)-5H-pyrrolo[3,2-d]pyrimidin-4-yl]-(1-ethyl-propyl)-amine $^1$H NMR (CDCl$_3$) ä 6.91(s, 2H), 6.76(s, 1H), 4.61(d, 1H, NH), 4.33(m, 1H), 4.04(s, 3H), 2.49(s, 3H), 2.28(s, 3H), 2.09(s, 6H), 1.72(m, 2H), 1.60(m, 2H), 0.98(t, 6H)ppm.

EXAMPLE 16

Butyl-[2,5-dimethyl-7-(2,4,6-trimethyl-phenyl)-5H-pyrrolo[3,2-d]pyrimidin-4-yl]-ethyl-amine $^1$H NMR (CDCl$_3$) ä 6.96(s, 1H), 6.92(s, 2H), 3.93(s, 3H), 3.44(q, 2H), 3.40(m, 2H), 2.57(s, 3H), 2.29(s, 3H), 2.09(s, 6H), 1.57(m, 2H), 1.30(m, 2H), 1.14(t, 3H), 0.88(t, 3H)ppm.

EXAMPLE 17

2,5-Dimethyl-4-thiazolidin-3-yl-7-(2,4,6-trimethyl-phenyl)-5H-pyrrolo[3,2-d]pyrimidine $^1$H NMR (CDCl$_3$) ä 7.03(s, 1H), 6.92(s, 2H), 4.78(s, 2H), 4.02(s, 3H), 3.96(m, 2H), 3.18(m, 2H), 2.56(s, 3H), 2.29 (3H), 2.06(s, 6H) ppm.

EXAMPLE 18

7-(1-Ethyl-propylamino)-1,5-dimethyl-3-(2,4,6-trimethyl-phenyl)-1H-pyrrolo[3,2-b]pyridine-6-carboxylic acid methyl ester $^1$H NMR (CDCl$_3$) ä 6.98(s, 1H), 6.93(s, 2H), 5.40(d, 1H), 3.97(s, 3H), 3.91(s, 3H), 3.35(m, 1H), 2.57(s, 3H), 2.30(s, 3H), 2.09(s, 6H), 1.52(m, 4H), 0.87(t, 6H) ppm.

EXAMPLE 19

7-(1-Ethyl-propylamino)-1,5-dimethyl-3-(2,4,6-trimethyl-phenyl)-1H-pyrrolo[3,2-b]-pyridine-6-carboxylic acid A mixture of 7-(1-ethyl-propylamino)-1,5-dimethyl-3-(2,4,6-trimethyl-phenyl)-1H-pyrrolo[3,2-b]pyridine-6-carboxylic acid methyl ester and NaOH in a 1:1 mixture of MeOH/water was heated at reflux over night. The resulting mixture was acidified with 2N HCl to a pH of 4–5, and extracted with chloroform. The organic layer was dried and concentrated to give the title compound.

$^1$H NMR (CDCl$_3$) ä 7.02(s, 1H), 6.82(s, 2H), 3.98(s, 3H), 3.78(m, 1H), 2.59(s, 3H), 2.07(s, 3H), 2.00(s, 6H), 1.64(m, 4H), 0.90(t, 6H) ppm.

EXAMPLE 20

[1,5-Dimethyl-3-(2,4,6-trimethyl-phenyl)-1H-pyrrolo[3,2-b]pyridin-7-yl]-(1-ethyl-propyl)-amine A mixture of 7-(1-ethyl-propylamino)-1,5-dimethyl-3-(2,4,6-trimethyl-phenyl)-1H-pyrrolo[3,2-b]pyridine-6-carboxylic acid was heated in 150–160° C. oil bath until all the starting material was consumed. $^1$H NMR (CDCl$_3$) ä 6.94(s, 2H), 6.87(s, 1H), 6.15(s, 1H), 6.10(d, 1H), 4.24(s, 3H), 3.50(m, 1H), 2.64(s, 3H), 2.30(s, 3H), 2.05(s, 6H), 1.77(m, 4H), 1.02(t, 6H)ppm.

PREPARATION A 4-(2,4,6-Trimethyl-phenyl)-2H-pyrazol-3-ylamine

A mixture of 3-oxo-2-(2,4,6-trimethyl-phenyl)-propionitrile (2.300 g, 12.3 mmol), hydrazine hydrate (0.93 g) and glacial acetic acid (1.55 ml) in 20 ml benzene was heated at reflux for 4.5 hours. Reaction mixture was cooled to room temperature and 50 ml of 18.5% HCl in water was added. The benzene layer was separated and reextracted with 18.5% HCl. The aqueous layer were combined and neutralized with ammonium hydroxide and stirred at rt. overnight. Precipitate formed and was filtered to yield the title compound (0.256 g) as a yellow solid. The benzene layer was concentrated and purified through silica gel column using 5% methanol in chloroform as eluent to give an additional 1.450 g of the title compound; $^1$H NMR (CDCl$_3$) ä 7.24(s, 1H), 6.95(s, 2H), 4.75(brs, 2H), 2.32(s, 3H), 2.13(s, 6H) ppm.

PREPARATION B

5-Methyl-4-(2,4,6-trimethyl-phenyl)-2H-pyrazol-3-ylamine

The title compound was prepared as white solid by the method analogous to that described in preparation A starting from 3-oxo-2-(2,4,6-trimethyl-phenyl)-butyronitrile. $^1$H NMR (CDCl$_3$) ä 7.7(brs, 1H), 6.96(s, 2H), 2.32(s, 3H), 2.13(s, 3H), 2.06(s, 6H) ppm.

PREPARATION C 2,5-Dimethyl-3-(2,4,6-trimethyl-phenyl)-4H-pyrazolo[1,5-a]pyrimidin-7-one Methyl acetoacetate (0.38 ml) was added to a solution of 5-methyl-4-(2,4,6-trimethyl-phenyl)-2H-pyrazol-3-ylamine (641 mg, 2.98 mmol) in 4 ml of acetic acid. The reaction mixture was heated at reflux for overnight. The mixture was concentrated to dryness and the residue was purified through silica gel column chromatography using 5% methanol in chloroform as eluent to give 560 mg (65.5%) of the title compound as a white solid;

$^1$H NMR (DMSO-d$_6$) ä 11.7(s, 1H), 6.98(s, 2H), 5.52(s, 1H), 2.29(s, 3H), 2.20(s, 3H), 1.97(s, 3H), 1.95(s, 6H) ppm.

PREPARATION D

5-Methyl-3-(2,4,6-trimethyl-phenyl)-4H-pyrazolo[1,5-a]pyrimidin-7-one

Methyl acetoacetate (0.7 ml) was added to a solution of 4-(2,4,6-Trimethyl-phenyl)-2H-pyrazol-3-ylamine (1.120 g, 5.57 mmol) in 5 ml of acetic acid and the resulting mixture was heated at reflux for two days. Reaction mixture cooled and a white solid formed. Ethanol (6 ml) was added and stirred at room temperature overnight, filtered to give white solid which was recrystallized from ethanol to give 673 mg(45.2%) of the title compound as white crystals. $^1$H NMR (DMSO-d$_6$) ä 11.9(s, 1H), 7.7(s, 1H), 6.95(s, 2H), 5.55(s, 1H), 2.25(s, 3H), 2.20(s, 3H), 2.0(s, 6H)ppm.

PREPARATION E

7-Chloro-5-methyl-3-(2,4,6-trimethyl-phenyl)-pyrazolo[1,5-a]pyrimidine

A suspension of 5-methyl-3-(2,4,6-trimethyl-phenyl)-4H-pyrazolo[1,5-a]pyrimidin-7-one (590 mg, 2.2 mmol) in 9 ml of POCl$_3$ was treated with diethylaniline (0.7 ml) and the resulting mixture was stirred at reflux for 15 hours. The reaction mixture was concentrated to dryness. The residue was treated with ice water and stirred for 20 min, then extracted with chloroform. The organic layer was dried and concentrated to yield an orange oil which crystallized upon standing. The material was purified through silica gel column chromatography using chloroform as eluent to give 590 mg (94%) of the title compound as a yellow solid; $^1$H NMR (CDCl$_3$) ä 8.08(s, 1H), 6.98(s, 2H), 6.86(s, 1H), 2.56(s, 3H), 2.33(s, 3H), 2.09(s, 6H) ppm.

PREPARATION F

7-Chloro-2,5-dimethyl-3-(2,4,6-trimethyl-phenyl)-pyrazolo[1,5-a]pyrimidine

The title compound was prepared as an oil by the method analogous to that described in preparation E starting from 2,5-dimethyl-3-(2,4,6-trimethyl-phenyl)-4H-pyrazolo[1,5-a]pyrimidin-7-one. $^1$H NMR (CDCl$_3$) ä 6.98(s, 2H), 6.77(s, 1H), 2.51(s, 3H), 2.33(s, 3H), 2.31(s, 3H), 1.99(s, 6H) ppm.

PREPARATION G

2,5-Dimethyl-7-(2,4,6-trimethyl-phenyl)-5H-pyrrolo[3,2-d]pyrimidin-4-ol

A mixture of 3-amino-1-methyl-4-(2,4,6-trimethylphenyl)-1H-pyrrole-2-carbonitrile (0.4 mmol) and acetic anhydride (0.043 ml) in acetic acid (0.01 ml) was heated at reflux untill all the starting material was consumed. The reaction mixture was concentrated to dryness. The residue was quenched with water and extracted with ethyl acetate. The organic extracts was washed with brine and concentrated to dryness. The residue was suspended in 0.5 ml of 85% phosphoric acid and heated at 130° C. for 1 hour. The mixture was cooled and poured into ice-water, stirred until solid formed. The solid was filtered to give 2,5-dimethyl-7-(2,4,6-trimethylphenyl)-5H-pyrrolo[3,2-d]pyrimidin-4-ol. The alternative way for the work up is via extraction technique. The ice water was extracted with chloroform. The organic layer was dried and concentrated to dryness to give the desired product.

$^1$H NMR ä (CDCl$_3$) 6.92(s, 2H), 6.88(s, 1H), 4.14(s, 3H), 2.43(s, 3H), 2.29(s, 3H), 2.09(s, 6H).

The following compounds can be prepared in a similar manner:

2,5-Dimethyl-7-(2,6-dimethyl-4-chloro-phenyl)-5H-pyrrolo[3,2-d]pyrimidin-4-ol;

2,5-Dimethyl-7-(2,6-dimethyl-4-bromo-phenyl)-5H-pyrrolo[3,2-d]pyrimidin-4-ol;

2-Methyl-7-(2,4,6-trimethyl-phenyl)-5H-pyrrolo[3,2-d]pyrimidin-4-ol;

2-Methyl-7-(2,6-dimethyl-4-chloro-phenyl)-5H-pyrrolo[3,2-d]pyrimidin-4-ol;

2-Methyl-7-(2,6-drimethyl-4-bromo-phenyl)-5H-pyrrolo[3,2-d]pyrimidin-4-ol; and

2-Methyl-7-(2,4,6-trimethyl-phenyl)-5H-pyrrolo[3,2-d]pyrimidin-4-ol;

PREPARATION H

4-Chloro-2,5-dimethyl-7-(2,4,6-trimethyl-phenyl)-5H-pyrrolo[3,2-d]pyrimidine A mixture of 2,5-dimethyl-7-(2,4,6-trimethylphenyl)-5H-pyrrolo[3,2-d]pyrimidin-4-ol (1 mmol) in POCl$_3$ (1.3 ml) was heated at reflux until all the starting material were consumed (about 1–3 hours). The mixture was concentrated to dryness. The residue was porued into ice-water and extracted with ethyl acetate. The organic layer was dried and concentrated to dryness to give the title compound.

$^1$H NMR (CDCl$_3$) ä 7.18(s, 1H), 6.95(s, 2H), 4.16(s, 3H), 2.69(s, 3H), 2.31(s, 3H), 2.05(s, 6H) ppm.

PREPARATION I

7-Amino-1,5-dimethyl-3-(2,4,6-trimethyl-phenyl)-1H-pyrrolo[3,2-b]pyridine-6-carboxylic acid methyl ester A mixture of 3-amino-1-methyl-4-(2,4,6-trimethylphenyl)-1H-pyrrole-2-carbonitrile (2 mmol), methyl acetoacetate (4 mmol) and SnCl$_4$ (4 mmol) in 1,2-dichloroethane was heated at reflux for about six hours until all the starting material were consumed. The mixture was quenched with acetone, basified with saturated NaHCO$_3$, then filtered through Celite?. The filtrate was concentrated to dryness. The residue was quenched with water and extracted with chloroform. The chloroform layer was washed with brine, dried and concentrated to dryness to give 7-amino-1,5-dimethyl-3-(2,4,6-trimethyl-phenyl)-1H-pyrrolo[3,2-b]pyridine-6-carboxylic acid methyl ester. The product may be purified by trituration.

$^1$H NMR (CDCl$_3$) ä 6.91(s, 2H), 6.85(s, 1H), 6.28(brs, 2H), 4.10(s, 3H), 3.89(s, 3H), 2.62(s, 3H), 2.28(s, 3H), 2.09(s, 6H) ppm.

PREPARATION J

7-Bromo-1,5-dimethyl-3-(2,4,6-trimethyl-phenyl)-1H-pyrrolo[3,2-b]pyridine-6-carboxylic acid methyl ester A mixture 7-amino-1,5-dimethyl-3-(2,4,6-trimethylphenyl)-1H-pyrrolo[3,2-b]pyridine-6-carboxylic acid methyl ester (1 mmol), n-butylnitrite (BuONO) (1.5 mmol) and CuBr$_2$ in acetonitrile was heated at 60–70° C. until all starting material was consumed. The mixture was quenched with water and extracted with ethyl acetate. The organic layer was dried and concentrated to dryness to give the title compound.

$^1$H NMR (CDCl$_3$) ä 7.09(s, 1H), 6.94(s, 2H), 4.16(s, 3H), 3.98(s, 3H), 2.52(s, 3H), 2.30(s, 3H), 2.04(s, 6H) ppm. 2,7-dibromo-1,5-dimethyl-3-(2,4,6-trimethyl-phenyl) 1H-pyrrolo[3,2-b]pyridine-6-carboxylic acid methyl ester was also produced as a minor component. $^1$H NMR (CDCl$_3$) ä 7.00(s, 2H), 4.45(s, 3H), 4.03(s, 3H), 2.51(s, 3H), 2.34(s, 3H), 2.12(s, 6H) ppm.

What is claimed is:

1. A compound of the formula

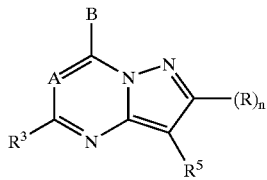

I-E or a pharmaceutically acceptable salt thereof, wherein

A is CR$^7$;

B is —CHR$^1$R$^2$, —NR$^1$R$^2$, —NHCHR$^1$R$^2$, —OCHR$^1$R$^2$, or —SCHR$^1$R$^2$;

R$^1$ is C$_1$–C$_6$ alkyl which may be optionally substituted with one hydroxy, fluoro, CF$_3$ or C$_1$–C$_4$alkyl, which may optionally contain one or two double or triple bond;

R$^2$ is benzyl or C$_1$–C$_6$alkyl, which may optionally contain one double or triple bond, wherein said C$_1$–C$_6$ alkyl and the phenyl moiety of said benzyl may optionally be substituted with one fluoro, CF$_3$, C$_1$–C$_2$ alkyl, C$_1$–C$_2$ alkoxy, or chloro group;

R$^3$ is hydrogen, C$_1$–C$_4$alkyl, —O(C$_1$–C$_4$alkyl), chloro, fluoro, bromo, iodo, (C$_1$–C$_2$ alkylene)-O—(C$_1$–C$_2$alkyl), (C$_1$–C$_2$alkylene)-OH, or —S(C$_1$–C$_4$alkyl);

n is zero to two;

each R is, independently, hydrogen, (C$_1$–C$_6$alkyl), fluoro, chloro, bromo, iodo, hydroxy, cyano, amino, (C$_1$–C$_2$alkylene)-OH, CF$_3$, CH$_2$SCH$_3$, nitro, —O(C$_1$–C$_4$alkyl), —N(C$_1$–C$_4$alkyl)(C$_1$–C$_2$alkyl), —S(C$_1$–C$_4$alkyl), —CO(C$_1$–C$_4$alkyl), —C(=O)H or —C(=O)O(C$_1$–C$_4$alkyl);

R$^5$ is phenyl, pyridyl, pyrazinyl, pyrimidyl, pyridazinyl and wherein each of the foregoing R$^5$ groups is substituted with from one to four R$^{13}$ substituents wherein one to three of said R$^{13}$ substituents may be selected, independently, from fluoro, chloro, C$_1$–C$_6$alkyl and —O(C$_1$–C$_2$alkyl) and one of said R$^{13}$ substituents may be selected from bromo, iodo, formyl, OH, (C$_1$–C$_4$alkylene)-OH, (C$_1$–C$_4$alkylene)-O—(C$_1$–C$_2$alkyl), —CN, —CF$_3$, —NO$_2$, —NH$_2$, —NH(C$_1$–C$_4$alkyl), —N(C$_1$–C$_2$alkyl)(C$_1$–C$_6$alkyl), —OCO(C$_1$–C$_4$alkyl), (C$_1$–C$_4$alkylene)-O—(C$_1$–C$_4$alkyl), —S(C$_1$–C$_6$alkyl), (C$_1$–C$_4$alkylene)-S—(C$_1$–C$_4$alkyl), —C(=O)O(C$_1$–C$_4$alkyl), —C(=O)(C$_1$–C$_4$alkyl), —COOH, —SO$_2$NH(C$_1$–C$_4$alkyl), —SO$_2$N(C$_1$–C$_2$alkyl)(C$_1$–C$_4$alkyl), —SO$_2$NH$_2$, —NHSO$_2$(C$_1$–C$_4$alkyl), —S(C$_1$–C$_6$alkyl) and —SO$_2$(C$_1$–C$_6$alkyl), and wherein each of the C$_1$–C$_4$alkyl and C$_1$–C$_6$alkyl moieties in foregoing R$^5$ groups may optionally have one or two double bonds;

R$^7$ is hydrogen, C$_1$–C$_1$alkyl, halo, hydroxy, —O(C$_1$–C$_4$alkyl, —C(=O)(C$_1$–C$_4$alkyl), —C(=O)(C$_1$–C$_4$alkyl), —OCF$_3$, —CF$_3$, —CH$_2$OH or —CH$_2$O(C$_1$–C$_2$ alkyl);

or the pharmaceutically acceptable salts of such compounds.

2. Compounds according to claim 1 wherein R$^3$ is methyl.

3. A compound according to claim 1, wherein R$^3$ is methyl, ethyl, chloro or methoxy.

4. A compound according to claim 1, wherein R$^4$ and R$^6$ selected from hydrogen, methyl and ethyl.

5. A compound according to claim 1, wherein R$^5$ is di- or tri-substituted phenyl, pyridyl, or pyrimidyl, in which the two or three substituents on said phenyl, pyridyl, or pyrimidyl are selected, independently, from C$_1$–C$_4$alkyl, —O—(C$_1$–C$_4$alkyl), (C$_1$–C$_2$alkyl)-O—(C$_1$–C$_4$alkyl), —CF$_3$, OCF$_3$, —CHO, —(C$_1$–C$_4$alkyl)—OH, cyano, chloro, fluoro, bromo, iodo, wherein each of the foregoing C$_1$–C$_4$alkyl groups may optionally contain one double or triple bond.

6. A compound selected from the group consisting of:

7-(1-ethyl-propoxy)-5-methyl-3-(2,4,6-trimethyl-phenyl)-pyrazolo[1,5-a]pyrimidine;

[2,5-Dimethyl-3-(2,4,6-trimethyl-phenyl)-pyrazolo[1,5-a]pyrimidin-7-yl]-(1-ethyl-propyl)-amine;

(1-Ethyl-propyl)-[5-methyl-3-(2,4,6-trimethyl-phenyl)-pyrazolo[1,5-a]pyrimidin-7-yl]-amine;

7-(1-Ethyl-propoxy)-2,5-dimethyl-3-(2,4,6-trimethyl-phenyl)pyrazolo[1,5-a]pyrimidine; and

[2,5-Dimethyl-3-(2,4,6-trimethyl-phenyl)-pyrazolo[1,5] pyrimidin-7-yl]-ethyl-propyl-amine;

or a pharmaceutically acceptable salt of such compound.

7. A pharmaceutical composition for the treatment, prevention or inhibition of a disorder selected from generalized anxiety disorder; panic; phobias; sleep disorders induced by stress; and depression in a mammal, comprising an amount of a compound according to claim 1 that is effective in the treatment of such disorder, and a pharmaceutically acceptable carrier.

8. The pharmaceutical composition of claim 7, wherein the disorder is depression.

9. A method for the treatment, prevention or inhibition of a disorder selected from generalized anxiety disorder; panic; phobias; sleep disorders induced by stress; and depression in a mammal, comprising administering to a subject in need of said treatment an amount of a compound according to claim 1, that is effective in treating such disorder.

10. The method of claim 9, wherein the disorder is depression.

* * * * *